United States Patent
Franks et al.

(10) Patent No.: US 7,390,508 B2
(45) Date of Patent: Jun. 24, 2008

(54) USE OF XENON WITH HYPOTHERMIA FOR TREATING NEONATAL ASPHYXIA

(75) Inventors: Nicholas Peter Franks, Highbury (GB); Mervyn Maze, London (GB)

(73) Assignee: Protexeon Limited, London (GB)

( * ) Notice: Subject to any disclaimer, the term of this patent is extended or adjusted under 35 U.S.C. 154(b) by 0 days.

(21) Appl. No.: 10/573,093

(22) PCT Filed: Oct. 11, 2004

(86) PCT No.: PCT/GB2004/004298

§ 371 (c)(1),
(2), (4) Date: Mar. 23, 2006

(87) PCT Pub. No.: WO2005/034966

PCT Pub. Date: Apr. 21, 2005

(65) Prior Publication Data

US 2007/0104796 A1  May 10, 2007

(30) Foreign Application Priority Data

Oct. 10, 2003 (GB) ................ 0323861.5
Aug. 19, 2004 (GB) ................ 0418539.3

(51) Int. Cl.
*A61K 33/00* (2006.01)
*A01N 59/00* (2006.01)
(52) U.S. Cl. .................... 424/600; 514/959
(58) Field of Classification Search .......... None
See application file for complete search history.

(56) References Cited

U.S. PATENT DOCUMENTS 5,099,834 A * 3/1992 Fishman ............. 128/203.12
6,197,323 B1 * 3/2001 Georgieff ................ 424/423
2002/0068764 A1  6/2002 Franks et al.

FOREIGN PATENT DOCUMENTS

DE  199 33 704 A1  1/2001
WO  WO 00/53192  9/2000

OTHER PUBLICATIONS

Ohashi et al. Anesthesiology 2002, 96, A1291.*
Taylor et al. Pediatric Research 2002, 51(1), 13-19.*
Chow et al. "Combined neuroprotection by xenon and hypothermia", Society for Neuroscience Abstract Viewer and Itinerary Planner, vol. 2003, 2003, pages Abstract No. 893.1 URL- http://sf. XP008042249.
Jacobs, et al. "Cooling for newborns with hypoxic ishaemic encephalopathy" Internet Article Online XP002315720, Retrieved from Internet.
Trescher et al. "Brief post-hypoxic-ishemic hypothermia markedly delays neonatal brain injury" Brain and Development, vol. 19, 1997, pp. 326-338, XP008042244, pp. 333, 336.
Goto, et al. "Thermoregulatory thresholds for vasoconstriction in patients anesthetized with various 1-minimum alveolar concentration combinations of xenon, nitrous oxide, and isoflurane", Anesthesiology, vol. 91, No. 3, 1999, pp. 626-632, XP002315721, p. 630.

* cited by examiner

*Primary Examiner*—Johann Richter
*Assistant Examiner*—Ernst V Arnold
(74) *Attorney, Agent, or Firm*—Kenyon & Kenyon LLP

(57) ABSTRACT

The present invention relates to the use of xenon in the preparation of a medicament for the treatment of neonatal asphyxia in a neonatal subject, wherein said medicament is for use in combination with hypothermia.

20 Claims, 16 Drawing Sheets

A.

B.

A.

B.

A.

B.

A.

B.

A.

B.

USE OF XENON WITH HYPOTHERMIA FOR TREATING NEONATAL ASPHYXIA

CROSS-REFERENCE TO RELATED APPLICATIONS

The present application is a 371 application of PCT/GB04/04298 and claims the benefit of UK Application No. 0323861.5, filed on Oct. 10, 2003 and UK Application No. 0418539.3 filed on Aug. 19, 2004.

The present invention relates to a method of treating neonatal asphyxia.

BACKGROUND TO THE INVENTION

Neonatal (or perinatal) asphyxia, also known as hypoxia-ischemia (HI), is a condition arising from the inadequate intake of oxygen in an infant during labour, delivery, or the immediate postnatal period. Neonatal asphyxia remains a major cause of chronic neurological morbidity and acute mortality in the newborn (Balduini et al, 2000; Vannucci et al, 1997) and commonly leads to hypoxic-ischemic encephalopathy.

Studies have shown that neonatal asphyxia (hypoxia) for as short a time as six minutes can lead to permanent neurological damage. Loss of brain tissue has been demonstrated in asphyxiated newborn primates and correlated with memory dysfunction and spastic paralysis (Windle, WF, 1969).

About 14.6% of all deaths at birth are caused by neonatal asphyxia. In the western world about 0.9% (i.e. 100-130,000) of newborns suffer from neonatal asphyxia. About 15-20% die, and of the survivors, 25% are severely handicapped due to long-term complications such as mental retardation, cerebral palsy, spasticity, learning difficulties and/or epilepsy (Law et al, 1993; Perlman et al. 1999). Furthermore, it is increasingly recognized that children with rather mild asphyxia, who seem initially to recover without complications, have behavioral problems in childhood, which can be traced back to this neonatal insult. Neonatal asphyxia meets the criteria for an orphan drug indication since it affects less then 5 patients in 10,000 inhabitants, and is a life-threatening, serious debilitating disease without an established therapy.

It has been demonstrated in neonatal animal models of HI that the mechanisms of cell death involved in this type of brain injury, involve a combination of excitotoxic damage (or necrosis), caused by excessive activation of glutamate receptors, particularly N-methyl-D-aspartate (NMDA) receptors, as they are most sensitive to neurotoxicity during periods of synaptogenesis (Jevtovic-Todorovic and Olney, 2003), and by apoptotic neurodegeneration (Ikonomidou et al, 1989; Pohl et al, 1999). The type of damage is related to the severity of the hypoxic insult (Jevtovic-Todorovic and Olney, 2003) and also to the variation in vulnerability of the different brain regions (Northington et al, 2001). Currently, no effective therapy exists to combat the acute neuronal cell death caused by HI, although a variety of both pharmacological and non-pharmacological interventions are under experimental investigation (Vannucci and Perlman, 1997).

The present invention seeks to provide a method of treating neonatal asphyxia.

STATEMENT OF INVENTION

A first aspect of the invention relates to the use of xenon in the preparation of a medicament for the treatment of neonatal asphyxia, wherein said medicament is for use in combination with hypothermia.

A second aspect of the invention relates to a method of treating neonatal asphyxia in a mammal in need thereof, said method comprising:
(a) administering a therapeutically effective amount of xenon to the mammal; and
(b) subjecting the mammal to hypothermia.

A third aspect of the invention relates to a method of treating neonatal asphyxia in a mammal in need thereof, said method comprising administering a therapeutically effective amount of xenon to the mammal in combination with hypothermia.

A fourth aspect of the invention relates to the use of xenon in the preparation of a medicament for the treatment of neonatal asphyxia, wherein said treatment comprises administering to a subject simultaneously, sequentially or separately xenon in combination with hypothermia.

A fifth aspect of the invention relates to the use of xenon, in combination with hypothermia, for the treatment of neonatal asphyxia.

DETAILED DESCRIPTION

Normal Physiology of the Immature CNS

The excitatory amino acids (EAAs) glutamate and aspartate are the chief mediators of excitatory synaptic transmission in the mature central nervous system (CNS) (Dingledine and McBain, 1999). They also play a pivotal role in the ontogeny of the immature CNS, where they are involved in a number of physiological processes such as synaptogenesis, neuronal survival, synaptic plasticity, and dendritic and axonal structure. However, excessive activation of these amino acid receptors during development can produce neuronal injury and death. This is termed 'excitotoxicity'.

Glutamate is the most abundant of the EAAs (Dingledine and McBain, 1999). It is stored in synaptic vesicles and causes calcium-dependent membrane depolarisation of postsynaptic membranes when it is released from the presynaptic terminals. Glutamate exerts its excitatory effect at a variety of receptor subtypes that can be divided into N-methyl-D-aspartate (NMDA) and non-NMDA types, but in the developing CNS it is the NMDA receptor subtype that has been found to play the primary role in brain injury associated with HI (Ikonomidou et al, 1989; Komuro, 1993; MacDonald et al, 1986).

The NMDA receptor is a major subclass of glutamate receptor and glutamate is believed to be the most important excitatory neurotransmitter in the mammalian central nervous system. Importantly, activation of the NMDA receptor has been shown to be the central event which leads to excitotoxicity and neuronal death in many disease states, as well as a result of hypoxia and ischaemia following head trauma, stroke and following cardiac arrest.

The NMDA receptor is an ionotropic receptor found ubiquitously throughout the CNS, located on the surface of both postsynaptic and extrasynaptic membranes (Riccio and Ginty, 2002; Sattler et al, 2000). It is coupled to a cationic channel that is permeable to both $Na^+$ and $Ca^{2+}$ ions and under normal physiological conditions, is blocked by $Mg^{2+}$ at a negative resting membrane potential. It becomes unblocked on depolarisation of the cell membrane, thus allowing an influx of $Ca^{2+}$ through the channel and enabling the receptor to exert its intracellular effects (Hardingham and Bading, 2003).

NMDA receptors are vital for normal brain function and their importance in normal physiology is demonstrated by their central role in memory and learning (Bliss and Collingridge, 1993). Conversely, pathological activation of NMDA receptors by excess glutamate is the primary cause of neuronal cell death following an ischaemic insult to the brain, due to the disruption of intracellular $Ca^{2+}$ regulation. This emphasizes the central role played by NMDA receptors in HI.

Hypoxic-Ischaemic Injury in the Neonate

In order for the brain to function, it requires a continuous supply of oxygen and glucose and is thus reliant on an adequate blood supply (Choi and Rothman, 1990). Should the blood supply become interrupted, as is the case in neonatal asphyxia, hypoxic-ischaemic damage to the area downstream will ensue within minutes. Under these conditions of oxygen depletion, cellular metabolism shifts from aerobic to anaerobic (Vannucci and Perlman, 1997), which is less effective at meeting the energy requirements of the cell. This leads to a depletion of energy stores, particularly affecting high-energy phosphate reserves such as ATP in the neuronal and glial cell compartments (Dingledine and McBain, 1999). There is concomitant accumulation of $H^+$ ions, leading to acidosis, and release of free radicals that contribute to further damage of the cells.

Under physiological conditions, the extracellular concentration of glutamate is maintained at low levels by the action of glutamate transporters located in neuronal cells, but expressed preferentially in glial cells (Dingledine and McBain, 1999). There are several different kinds of glutamate uptake carrier, but essentially, they all function in the same way, transporting two $Na^+$ cations and one glutamate anion into the cell, while transporting one $K^+$ cation and one $OH^-$ anion out of the cell and into the extracellular space (Dingledine and McBain, 1999). These ionic pumps act against an electrochemical gradient and thus rely on energy in the form of ATP in order to function correctly. Therefore, the ability of these pumps to maintain the resting membrane potential is decreased by the reduction in the concentration of ATP that results from HI. Consequently, failure of the ATP-dependent pump leads to depolarisation of the membrane, and a reversal in the direction of pumping (Eilers and Bickler, 1996; Kauppinen et al, 1988). Thus, glutamate is transported out of the cell and an excess concentration of glutamate accumulates in the extracellular space. Not only does the glutamate concentration increase due to a decreased uptake, but there is also an increased release of glutamate from the presynaptic terminals as the membrane depolarisation sets up an action potential (Dingledine and McBain, 1999). Examples of these processes leading to excess extracellular glutamate have been seen both in vitro (Bosley et al, 1983; Hauptman et al, 1984; Pellegrino-Giampietro et al, 1990) and in vivo (Erecinska et al, 1984; Graham et al, 1990; Ikeda et al, 1989).

Excitotoxicity occurs when the excess extracellular glutamate continuously activates postsynaptic receptors (particularly NMDA receptors) and the resulting calcium influx sets up an osmotic gradient down which water moves causing the cells to swell. Calcium-dependent enzyme systems are also activated within the cell and these two processes result in acute neuronal cell death (Choi and Rothman, 1990).

Mechanisms of Cell Death

Neuronal cell death has always been thought to arise from one of two mechanisms: necrosis and apoptosis, as hypothesised by Wyllie et al (Wyllie et al, 1980). However, recently these categories have been questioned as more evidence has come to light to suggest that cell death should be divided into the categories: excitotoxic cell death and apoptosis (Olney, 2003). Excitotoxic cell death has been described as a necrotic process (Gwag et al, 1997; Katja and Green, 2001), an apoptotic process, and a continuum of the two (Leist and Nicotera, 1998; Nakajima et al, 2000). Apoptosis and necrosis are usually distinguished by their distinctly different morphological appearances. Apoptosis requires ATP and new protein synthesis, and is identified by cell shrinkage, chromatin-clumping with margination and formation of membrane-enclosed apoptotic bodies, whereas necrosis is recognised by nuclear shrinkage with karyorrhectic and pyknotic nuclear changes (Hill et al, 1995).

Cell death from HI has been found to involve an initial period of necrosis, followed by a delayed wave of apoptotic cell death (Northington et al, 2001). The type of injury that ensues appears to be both time-dependent and location-dependent, with the initial necrotic injury being confined to the ipsilateral forebrain in a neonatal rat model of HI, and the delayed apoptotic injury occurring in the thalamus (Northington et al, 2001). This suggests that the different brain regions may express differential vulnerability to each type of cell death at different times following HI.

In normal development, apoptosis is a regular event by which unwanted or damaged neurons 'commit suicide' (Ikonomidou et al, 2001). In HI, the initial excitotoxic cell death is mediated by excessive activation of NMDA receptors, resulting in the uncontrolled release of glutamate, which damages the surrounding neurons. The natural response to damage during synaptogenesis is for the neurons to initiate programmed cell death (Olney, 2003), and this is thought to be a mechanism that is activated to protect the neighbouring tissue (Leist and Nicotera, 1998).

Xenon as a Neuroprotectant

It is known in the art that the NMDA receptor plays a major role in the synaptic plasticity which underlies many higher cognitive functions, such as memory and learning, as well as in certain nociceptive pathways and in the perception of pain (Collingridge et al, The NMDA Receptor, Oxford University Press, 1994). In addition, certain properties of NMDA receptors suggest that they may be involved in the information-processing in the brain which underlies consciousness itself.

NMDA receptor antagonists are therapeutically valuable for a number of reasons. Firstly, NMDA receptor antagonists confer profound analgesia, a highly desirable component of general anaesthesia and sedation. Secondly, NMDA receptor antagonists are neuroprotective under many clinically relevant circumstances (including ischemia, brain trauma, neuropathic pain states, and certain types of convulsions). Thirdly, NMDA receptor antagonists confer a valuable degree of amnesia.

Given the importance of NMDA receptors in the pathogenesis of HI, it is fitting that NMDA antagonists have been investigated as possible neuroprotective agents. Many NMDA antagonists, such as MK-801 and ketamine have been shown to be neuroprotective in both in vitro and in vivo models (Albers et al, 1989; Arias et al, 1999; Choi et al, 1988; Kudo et al, 2001). However, despite these encouraging results, NMDA receptor antagonists have also been shown to have psychotomimetic side effects in humans (Krystal et al, 1994) and to cause damage to the posterior cingulate (PC) and retrosplenial cortices (RS) (Olney et al, 1991). In addition, many conventional NMDA receptor antagonists lead to the production of involuntary movements, stimulation of the sympathetic nervous system, induction of neurotoxicity at high doses (which is pertinent since NMDA receptor antagonists have low potencies as general anaesthetics), depression of the myocardium, and proconvulsions in some epileptogenic paradigms e.g., "kindling" (Wlaz P et al, Eur. J. Neurosci. 1994; 6:1710-1719). There have also been considerable difficulties in developing new NMDA receptor antagonists that are able to cross the blood-brain barrier.

Xenon is an apolar, inert gas that is a potent NMDA antagonist (Franks et al, 1998). Like other NMDA antagonists, it has also been shown to be neuroprotective against many forms of neuronal injury, both in vitro (Petzelt et al, 2003) and in vivo (Homi et al, 2003; Wilhelm et al, 2002). However, unlike many of the other NMDA receptor antagonists, xenon is not neurotoxic (Ma et al, 2002). A further advantage of using xenon as an NMDA antagonist is that the molecule is an inert, volatile gas that can be rapidly eliminated via respiration.

Xenon has many other favourable properties. Since its first use in surgery (Cullen S C et al, Science 1951; 113:580-582), a number of research groups have shown it has an excellent pharmacological profile, including the absence of metabolic by-products, profound analgesia, rapid onset and recovery, and minimal effects on the cardiovascular system (Lachmann B et al, Lancet 1990; 335:1413-1415; Kennedy R R et al, Anaesth. Intens. Care 1992; 20:66-70; Luttropp H H et al, Acta Anaesthesiol. Scand. 1994; 38:121-125; Goto T et al, Anesthesiology 1997; 86:1273-1278; Marx T et al, Br. J. Anaesth. 1997; 78:326-327). Moreover, as xenon is a small, uncharged atom, it can easily pass through the blood-brain barrier thus producing a rapid onset of action (Nakata et al, 2001). It also has a very low blood: gas partition coefficient lending to fast emergence from xenon anaesthesia (Goto et al, 1997). As well as these advantages, xenon is non-explosive, non-toxic and unreactive (Shichino et al, 2002), and this makes xenon an ideal candidate for use as a neuroprotectant in the neonate.

As used herein, the term "neuroprotectant" means an agent that is capable of providing neuroprotection, i.e., protecting a neural entity, such as a neuron from ongoing injury from, for example, an ischaemic injury or traumatic injury.

Hypothermia as a Neuroprotectant

Talbot first demonstrated the neuroprotective properties of hypothermia for surgical use in 1941 (Talbot, 1941). Currently, the only routine use of hypothermia is during cardiopulmonary bypass to protect the brain from intra-operative ischaemia. However, there have been several publications demonstrating the therapeutic effect of hypothermia in other models of brain injury. For example, numerous publications exist showing the beneficial effect of hypothermia in both in vitro (Onitsuka et al, 1998) and in vivo models of neonatal asphyxia (Debillon et al, 2003; Treschera et al, 1997). It has been demonstrated that a direct correlation exists between tissue injury and the extent of brain cooling (Towfighi et al, 1994), and in normoxic conditions, every 1° C. decrease in body temperature leads to a 5% decrease in the cerebral metabolic rate (Yager and Asselin, 1996).

The mechanism by which hypothermia exerts its neuroprotective effect has yet to be elucidated, but many theories have been postulated. Studies have suggested that the mechanisms by which hypothermia is protective are temperature and time-dependent, and may act at more than one point along the cascade of events that leads to HI injury (Yager and Asselin, 1996). This is supported by the fact that a moderate temperature of 31° C. has been shown to be neuroprotective by decreasing cerebral energy metabolism, whereas a mild hypothermia of 34° C. while also neuroprotective, has no effect on energy metabolism and must therefore act via a different mechanism (Yager and Asselin, 1996). Another study by Taylor et al (Taylor et al, 2002) demonstrated that hypothermia instituted after the HI insult was more effective than intra-ischaemic hypothermia, and suggested that this may be due to a decrease of deleterious effects that occur during the recovery period. An example of one such mechanism could be that hypothermia decreases the excitotoxic damage that ensues during reperfusion (Taylor et al, 2002). Many other mechanisms of protection by hypothermia have been suggested, including the reduction of reactive oxygen species (Taylor et al, 2002), a reduction in tissue acidosis (Chopp et al, 1989) and the attenuation of post-HI neuronal apoptosis (Xu et al, 2002).

Xenon and Hypothermia in Combination

As mentioned above, a first aspect of the present invention relates to the use of xenon in the preparation of a medicament for the treatment of neonatal asphyxia in a neonatal subject, wherein said medicament is for use in combination with hypothermia.

As used herein, the term "hypothermia" refers to subjecting a particular subject (in this case, a neonatal subject) to hypothermic conditions, for example, by lowering the body temperature, preferably by 3-5° C., through passive or active techniques. Typically, subjecting to hypothermic conditions leads to a decrease in metabolism of body tissues of the subject, thereby decreasing the need for oxygen.

As mentioned above, the use of hypothermia in the treatment of neonatal asphyxia has been well documented in the art (see for example, Volpe, 2001; Gunn et al, 2000). However, to date there has been no teaching or suggestion in the art that hypothermia could be use in combination with the administration of xenon. Nor has there been any suggestion that such combination therapy would lead to such a surprising and unexpected enhancement in the resulting neuroprotective effect.

Previous studies by the applicant have revealed that xenon has neuroprotective properties. In particular, WO 01/08692, the contents of which are incorporated herein by reference, relates to the use of xenon as a neuroprotectant and/or as an inhibitor of synaptic plasticity. However, there is no teaching or suggestion in the prior art that xenon would be effective as a neuroprotectant in the context of the presently claimed invention.

In one preferred embodiment of the invention, the xenon is admixed with a pharmaceutically acceptable diluent, excipient or carrier.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers and dyes may be provided in the pharmaceutical composition. Examples of preservatives include sodium benzoate, sorbic acid and esters of p-hydroxybenzoic acid. Antioxidants and suspending agents may be also used.

The present invention is also applicable to the treatment of animals. In this regard, the invention further relates to the use of xenon in combination with: a veterinarily acceptable diluent, excipient or carrier.

For veterinary use, the xenon is typically administered in accordance with normal veterinary practice and the veterinary surgeon will determine the dosing regimen and route of administration which will be most appropriate for a particular animal.

The xenon may also be administered in combination with another pharmaceutically active agent. The agent may be any suitable pharmaceutically active agent including anaesthetic or sedative agents which promote GABAergic activity. Examples of such GABAergic agents include isoflurane, propofol and benzodiazapines.

In one preferred embodiment, the xenon is administered in combination with a volatile anesthetic agent, preferably isoflurane, sevoflurane or desflurane.

The xenon may also be administered in combination with other active ingredients such as L-type calcium channel blockers, N-type calcium channel blockers, substance P antagonists, sodium channel blockers, purinergic receptor blockers, or combinations thereof.

The xenon may be administered by any suitable delivery mechanism, or two or more suitable delivery mechanisms.

In one particularly preferred embodiment, the xenon is administered by perfusion. In the context of the present invention, the term "perfusion" refers to the introduction of an oxygen/xenon mixture into, and the removal of carbon dioxide from, a patient using a specialised heart-lung machine. In general terms, the heart-lung machine replaces the function of the heart and lungs and provides a bloodless, motionless surgical field for the surgeon. The perfusionist ventilates the patient's blood to control the level of oxygen and carbon dioxide. In the context of the present invention, the perfusionist also introduces xenon into the patient's blood. The perfusionist then propels the blood back into the arterial system to provide nutrient blood flow to all the patient's vital organs and tissues during surgery.

In one particularly preferred embodiment, the medicament is in gaseous form.

In another highly preferred embodiment, the xenon is administered by inhalation. More preferably, the xenon is administered by inhalation of a 70-30% v/v xenon/oxygen mixture.

More preferably, the xenon is administered in the form of a 20-70% v/v xenon/air mixture.

In yet another preferred embodiment of the invention, the medicament is in the form of a liquid or solution.

Preferably, the liquid is administered in the form of a solution or an emulsion prepared from sterile or sterilisable solutions, which may be injected intravenously, intraarterially, intrathecally, subcutaneously, intradermally, intraperitoneally or intramuscularly.

In one particularly preferred embodiment, the xenon is administered in the form of a lipid emulsion. The intravenous formulation typically contains a lipid emulsion (such as the commercially available Intralipid®10, Intralipid®20, Intrafat®, Lipofundin®S or Liposyn® emulsions, or one specially formulated to maximise solubility) which sufficiently increases the solubility of the xenon to achieve the desired clinical effect. Further information on lipid emulsions of this sort may be found in G. Kleinberger and H. Pamperl, Infusionstherapie, 108-117 (1983) 3.

The lipid phase of the present invention which dissolves or disperses the gas is typically formed from saturated and unsaturated long and medium chain fatty acid esters containing 8 to 30 carbon atoms. These lipids form liposomes in aqueous solution. Examples include fish oil, and plant oils such as soya bean oil, thistle oil or cottonseed oil. The lipid emulsions of the invention are typically oil-in-water emulsions wherein the proportion of fat in the emulsion is conventionally 5 to 30% by weight, and preferably 10 to 20% by weight. Oil-in-water emulsions of this sort are often prepared in the presence of an emulsifying agent such as a soya phosphatide.

The lipids which form the liposomes of the present invention may be natural or synthetic and include cholesterol, glycolipids, sphingomyelin, glucolipids, glycosphingolipids, phosphatidylcholine, phosphatidylethanolamine, phosphatidyl-serine, phosphatidyglycerol, phosphatidylinositol.

The lipid emulsions of the present invention may also comprise additional components. These may include-antioxidants, additives which make the osmolarity of the aqueous phase surrounding the lipid phase isotonic with the blood, or polymers which modify the surface of the liposomes.

It has been established that appreciable amounts of xenon maybe added to a lipid emulsion. Even by the simplest means, at 20° C. and normal pressure, xenon can be dissolved or dispersed in concentrations of 0.2 to 10 ml or more per ml of emulsion. The concentration of dissolved gas is dependent on a number of factors, including temperature, pressure and the concentration of lipid.

The lipid emulsions of the present invention may be loaded with gaseous xenon. In general, a device is filled with the emulsion and anaesthetics as gases or vapours passed through sintered glass bubblers immersed in the emulsion. The emulsion is allowed to equilibrate with the anaesthetic gas or vapour at a chosen partial pressure. When stored in gas tight containers, these lipid emulsions show sufficient stability for the anaesthetic not to be released as a gas over conventional storage periods.

The lipid emulsions of the present invention may be loaded so that the xenon is at the saturation level. Alternatively, the xenon may be present in lower concentrations, provided, for example, that the administration of the emulsion produces the desired pharmaceutical activity.

The concentration of xenon employed in the invention may be the minimum concentration required to achieve the desired clinical effect. It is usual for a physician to determine the actual dosage that will be most suitable for an individual patient, and this dose will vary with the age, weight and response of the particular patient. There can, of course, be individual instances where higher or lower dosage ranges are merited, and such are within the scope of this invention.

Preferably, the medicament is in a form suitable for intravenous, neuraxial or transdermal delivery.

Preferably, the xenon is administered simultaneously, in combination, sequentially or separately with hypothermia.

As used herein, "simultaneously" is used to mean that the xenon is administered concurrently with hypothermia, whereas the term "in combination" is used to mean the xenon is administered, if not simultaneously, then "sequentially" within a timeframe in which the xenon and the hypothermia both exhibit a therapeutic effect, i.e. they are both are available to act therapeutically within the same time-frame. Thus, administration "sequentially" may permit the xenon to be administered within 5 minutes, 10 minutes or a matter of hours before the hypothermia, provided the circulatory half-life of the xenon is such that it is present in a therapeutically effective amount when the neonatal subject is exposed to hypothermic conditions.

In another preferred embodiment of the invention, the neonate is subjected to hypothermia prior to treatment with xenon.

In contrast to "in combination" or "sequentially", "separately" is used herein to mean that the gap between administering the xenon and exposing the neonatal subject to hypothermia is significant i.e. the xenon may no longer be present in the bloodstream in a therapeutically effective amount when the neonatal subject is exposed to hypothermic conditions.

In one preferred embodiment, the xenon is administered sequentially with hypothermia.

More preferably, the xenon is administered sequentially before the hypothermia.

In another preferred embodiment, the xenon is administered separately before the hypothermia.

In one preferred embodiment, the xenon is administered sequentially after the hypothermia.

In another preferred embodiment, the xenon is administered separately after the hypothermia.

More preferably, the xenon is administered sequentially or simultaneously with hypothermia, more preferably simultaneously.

In one preferred embodiment of the invention, the xenon is administered in a therapeutically effective amount.

In another preferred embodiment, the xenon is administered in a sub-therapeutically effective amount. In other words, the xenon is administered in an amount that would be insufficient to produce the desired therapeutic effect if administered in the absence of hypothermic conditions.

Even more preferably, the combination of xenon and hypothermia has a synergistic effect, i.e., the combination is synergistic.

In one particularly preferred embodiment, the xenon is administered prior to the hypoxic insult. Thus, in one preferred embodiment, the xenon is administered to the neonate via the mother prior to birth, for example, by administering to the mother prior to or during labour. Preferably, the xenon is administered to the mother for up to about 48 or 24 hours prior to birth, more preferably up to about 12 hours, more preferably up to about 6 hours or 3 hours or 1 hour prior to birth. After birth, the neonate is then subjected to hypothermic conditions.

Another aspect of the invention relates to a method of treating neonatal asphyxia in a mammal in need thereof, said method comprising:
(a) administering a therapeutically effective amount of xenon to the mother of the mammal prior to and/or during labour; and
(b) subjecting the mammal to hypothermia after birth.

Preferably, the hypothermia is maintained for a period of at least about 6 hours, more preferably at least about 12 hours, after the hypoxic-ischemic (HI) insult.

In one preferred embodiment, the hypothermia is maintained for a period of from about 6 to about 24 hours after the hypoxic-ischemic (HI) insult.

Preferably, the hypothermia is maintained for a period of at least about 6 hours, more preferably at least about 12 hours, after birth.

In one preferred embodiment, the hypothermia is maintained for a period of from about 6 to about 24 hours after birth.

Preferably, treatment in accordance with the method of the invention is initiated within about 6 hours of the hypoxic-ischemic (HI) insult, and more preferably within about 2 hours of the hypoxic-ischemic insult.

Hypothermia may be produced passively, by allowing the temperature to drift downwards and not purposefully sustain body temperature. Being poikilothermic, neonates rapidly assume the temperature of their surroundings. Alternatively the patient may be actively rendered hypothermic by deliberately reducing their ambient temperature.

A second aspect of the invention relates to a method of treating neonatal asphyxia in a mammal in need thereof, said method comprising:
(a) administering a therapeutically effective amount of xenon to the mammal; and
(b) subjecting the mammal to hypothermia, or hypothermic conditions.

In a preferred embodiment, the mammal is a newborn subject in the first four weeks after birth. More preferably, the mammal is in the first two weeks, more preferably still, the first week after birth.

Preferably, the mammal is a human.

Preferably, the mammal is subjected to conditions of mild hypothermia. As used herein, the term "mild hypothermia" typically refers to a decrease in the core temperature from 37° C. to about 33° C.

In one preferred embodiment, the temperature of the mammal is maintained at a temperature of from about 31° C. to about 36° C.

More preferably, the temperature of the mammal is maintained at a temperature of from about 32° C. to about 36° C., more preferably from about 32° C. to about 35° C., more preferably still from about 33° C. to about 35° C.

Preferred embodiments for the second aspect of the invention are the same as those described above in respect of the first aspect.

Another aspect of the invention relates to a method of treating neonatal asphyxia in a mammal in need thereof, said method comprising administering a therapeutically effective amount of xenon to the mammal in combination with hypothermia. Yet another aspect of the invention relates to the use of xenon in the preparation of a medicament for the treatment of neonatal asphyxia, wherein said treatment comprises administering to a subject simultaneously, sequentially or separately xenon in combination with hypothermia.

A further aspect of the invention relates to the use of xenon, in combination with hypothermia, for the treatment of neonatal asphyxia.

In Vivo Studies

Using an animal model of HI, neonatal rats were exposed to treatment with xenon and hypothermia independently of each other. Xenon was shown to be neuroprotective against HI in the neonate by reducing the amount of apoptotic cell death, while hypothermia appeared less effective. In combination, xenon and hypothermia were neuroprotective via an anti-apoptotic mechanism (FIG. 17). Their combined effect was found to be synergistic.

The neonatal rat HI model is very established and has been validated for use in a number of previous studies (Levine, 1960; Rice et al, 1981). The age of the rats used in this model has been found to correspond to the brain maturity of the term human neonate (Clancy et al, 2001; Ikonimidou et al, 1989) and thus a reasonably accurate comparison can be made between the two.

During the hypothermia experiments, the temperature of the rat pups was monitored using a probe that was inserted into the cortex of one of the pups. The probe took approximately 15 minutes to equilibrate and this was allowed for by delaying the start time of the experiment until the probe began recording the correct temperature. There were fluctuations in temperature around the mean value, but these were controlled by continuous monitoring and manual adjustment of the water bath as necessary. Only one rat per group was monitored for temperature in order to minimise the trauma caused to the rats and also the damage inflicted upon the cortex by the probe; rats with the probe inserted could not be used for histological analysis.

The anaesthetic gas xenon has been shown to exhibit neuroprotection in several models of adult neuronal injury. Currently, no published data exist to confirm the same neuroprotective effect of xenon in neonates. The results of this study corroborate previous findings that xenon has significant neuroprotective properties and in addition, suggest that this neuroprotection extends to neonatal models of brain injury induced by hypoxia-ischaemia.

It has long been known that the activation of the NMDA subtype of glutamate receptors is required to sustain ongoing neuronal injury and death in HI, and it is well documented that xenon exerts its analgesic and anaesthetic effect via blockade of these receptors, thus it has been postulated that xenon's neuroprotective properties are as a result of this antagonism. Previously, several other NMDA antagonists have demonstrated neuroprotection in in vitro studies, but have subsequently failed when utilised in clinical settings (Muir and Lees, 1995). The reason behind these clinical failures is unknown, however it is possible that blockade of the glutamate receptor subtype is insufficient to protect against injury, which would imply that xenon exerts its neuroprotective effect through another mechanism.

In the present study, it has been demonstrated that xenon significantly protects against neonatal HI via an anti-apoptotic mechanism. Both apoptosis and necrosis are important components of neuronal loss after HI injury, but apoptosis appears to be the more important type of cell death in determining neonatal outcome (Taylor et al, 1999). Apoptotic death is often preceded by the activation of many genes, (including transcription factors) which may be either pro-apoptotic or anti-apoptotic. As xenon appears to interfere with apoptotic cell death, it is possible that it may exert its effect on one of these genes, or at some point along the apoptotic pathway. Currently, there is evidence for two different apoptosis pathways: the extrinsic pathway, and the intrinsic pathway. The extrinsic pathway (also referred to as the "death receptor pathway") involves the binding of cytokines to death receptors which activate caspase-8 and this in turn, activates the "executor caspsase", caspase-3, which goes on to induce apoptotic cell death (Mehmet, 2000). The intrinsic pathway is heavily dependent on mitochondria and involves an increase in mitochondrial membrane permeability caused by the pro-apoptotic protein bax. This leads to the release of cytochrome c, the formation of a complex of cytochrome c, Apaf-1 (apoptosis protease-activating factor-1) and caspase-9, and the subsequent activation of caspase-3. It is entirely possible that xenon acts on either one of these pathways, but there is evidence to suggest that apoptotic neurodegeneration induced by HI is mediated via the mitochondrial pathway and the initiation of bax-dependent mitochondrial changes (Taylor et al, 1999). Further to this, the NMDA antagonist ketamine has been shown to protect against incomplete cerebral ischaemia and reperfusion by early modulation of the balance between pro- and anti-apoptotic proteins, namely by inhibiting the HI-induced bax increase (Engelhard et al, 2003). Thus it is possible that xenon could inhibit apoptosis by downregulating bax. Bcl-2 is an anti-apoptotic protein that acts to decrease the permeability of the mitochondria and hence inhibit the release of cytochrome c. Its overexpression has been shown to decrease neuronal damage caused by transient global cerebral ischaemia in gerbils (Engelhard et al, 2003). Therefore, the upregulation of bcl-2 is another potential target for xenon. As xenon is apolar and fat soluble, it is able to distribute itself widely throughout the body. It can penetrate membranes and consequently, it may also have an effect in the nucleus by altering gene transcription to upregulate survival pathways, or inhibiting the RNA and protein synthesis of pro-apoptotic molecules.

Anti-necrosis by xenon was shown to be statistically significant in the cortex at 48 h, but not in the gyrus (FIG. 16). At all other time groups, xenon was not anti-necrotic. One possible explanation for this is that in accordance with a previous study (Northington et al, 2001), there is a secondary wave of necrotic cell death at 48 h that is only apparent in the cortex. This would explain the increase in the percentage of necrotic cells present in the positive controls at 48 h, compared with 16 and 24 h. Although it is not certain how xenon exerts an anti-necrotic effect in the cortex at 48 h, it may be that while xenon is unable to prevent necrosis that occurs before its administration (as in the 16 and 24 h groups), it is some how able to combat the secondary necrotic wave that occurs after its administration. Initial necrosis occurs as early as 3 h after the HI insult (Northington et al, 2001) and at this point xenon has not yet been administered. It is therefore unlikely to be able to arrest or reverse a process that has already occurred. However, the secondary necrotic wave occurs at a time at which xenon has been present in the brain for 48 h, and this suggests that the presence of xenon at the advent of necrosis may be able to decrease this type of cell death. Further work must to be completed to ascertain the exact mechanism of this interaction.

Previous studies have demonstrated that mild hypothermia of 33° C. is neuroprotective against ischaemic neuronal injury (Busto et al, 1987). Other studies have suggested that this neuroprotection is achieved via an anti-apoptotic mechanism (Xu et al, 2002). Experiments showed that there was no neuroprotection at 16 or 24 h (FIGS. 13 and 15 respectively).

At 48 h however, significant neuroprotection was achieved in both the cortex and the gyrus, but by different mechanisms. In the cortex, hypothermia is anti-necrotic and in the gyrus, it is anti-apoptotic (FIG. 16). The data in this study do not explain this effect, but one possible justification could be that different brain regions express differential vulnerability (Northington et al, 2001). In the cortex, the secondary necrotic wave (discussed above) occurs at a time at which hypothermia has already been administered, and this may make it more effective. In the gyrus however, there is no delayed necrosis and thus no anti-necrotic effect is observed. Anti-apoptosis appears to be the neuroprotective mechanism in this region, and it is possible that the expected anti-apoptotic neuroprotective effect of hypothermia, that is not evident at the earlier time intervals, may be exposed after longer periods.

The results demonstrated that when used in combination, 20% xenon and 35° C. hypothermia provided an astounding level of neuroprotection. As these values provided no neuroprotection when each agent was used alone, the result could not be explained by an additive mechanism, but instead had to be due to synergistic interaction between the two agents.

By way of summary, the present study has shown using an in vivo rat model to show that xenon is neuroprotective in the neonate, and significantly protects against apoptosis induced by hypoxic-ischaemic injury. The data in this study also suggest that when xenon and hypothermia are used in combination in the same model, they interact synergistically to dramatically decrease apoptotic cell death. Accordingly, this combination may represent an effective treatment to protect against the devastating neurological consequences of neonatal asphyxia.

The present invention is further described by way of example, and with reference to the following figures, wherein.

Figure 6:
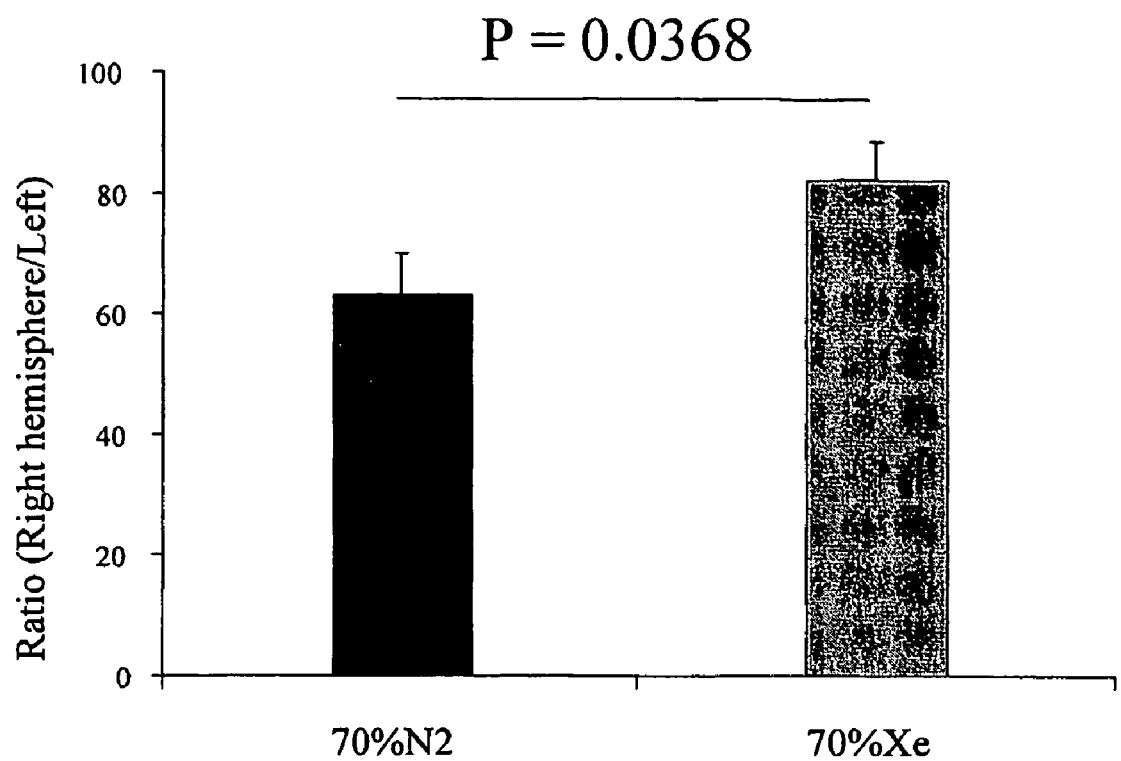

FIG. 6 compares the neuroprotective effect (ratio of right hemisphere/left) observed with $N_2$ and xenon respectively, when xenon is administered 2 hours post HI insult.

Figure 7:
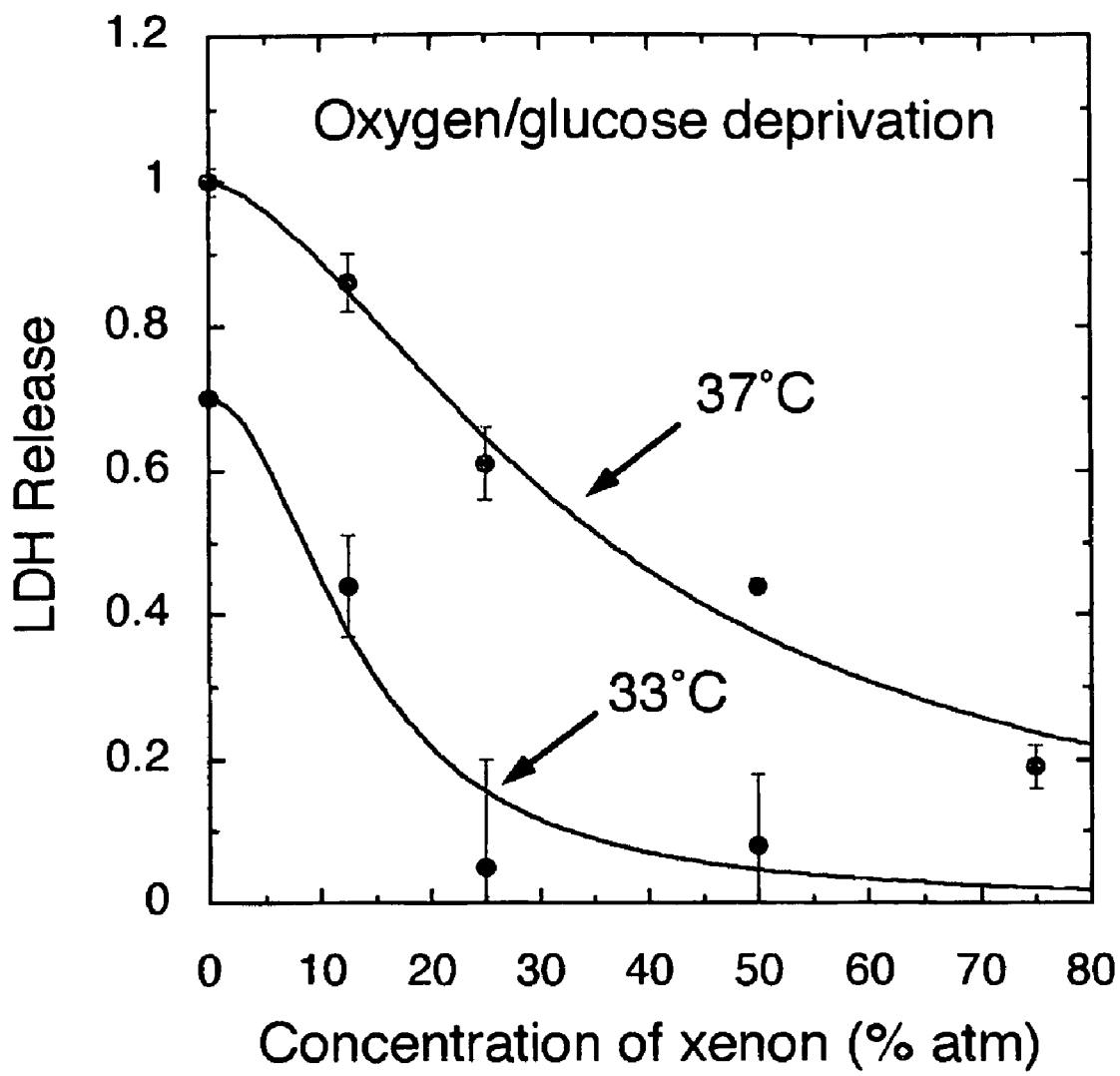

FIG. 7 shows the effect of mild hypothermia on the neuroprotective effect of xenon (LDH release against xenon concentration, % atm).

Figure 8:
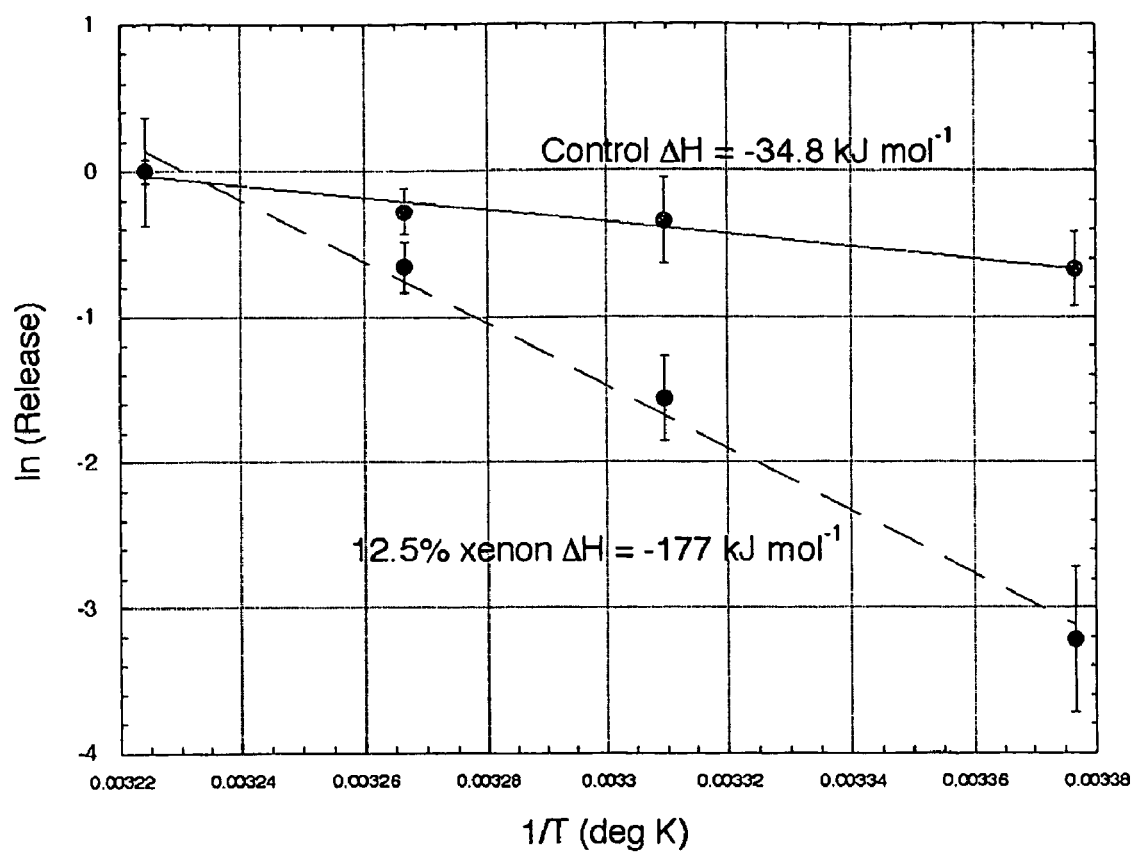

FIG. 8 shows a van't Hoff plot of the natural logarithm of LDH release plotted against reciprocal absolute temperature.

Figure 9:
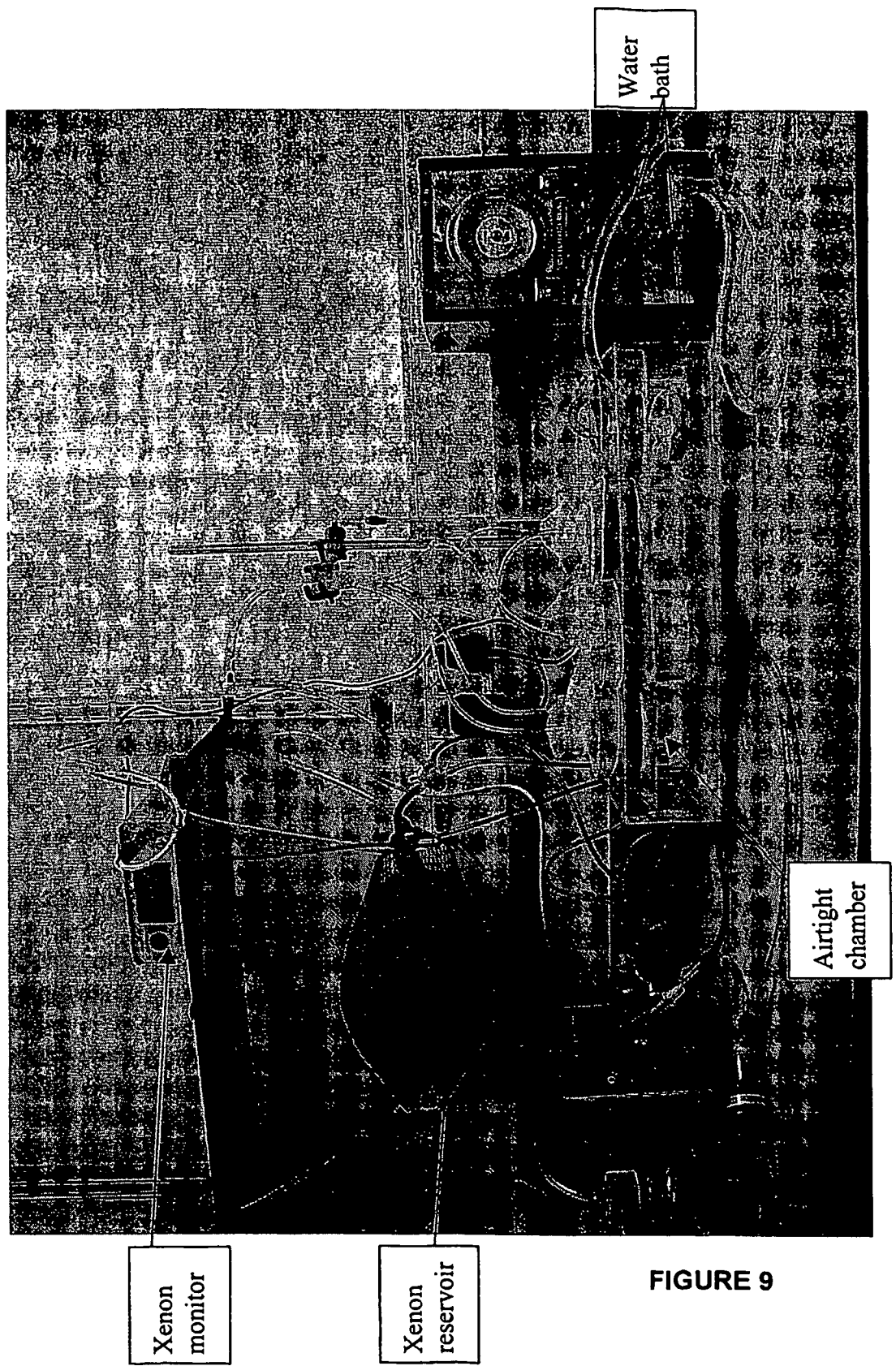

FIG. 9 shows a photograph of the purpose-built airtight chambers used for gas delivery. The water bath and closed circuit xenon delivery system are also depicted.

Figure 10:
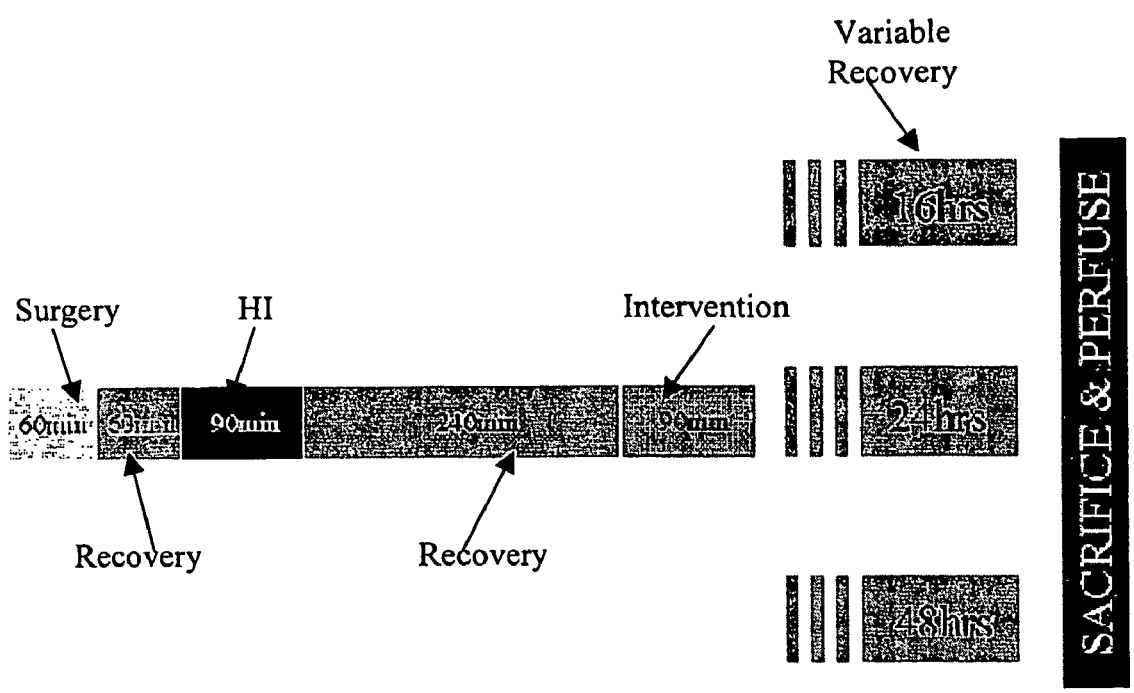

FIG. 10 shows a schematic timeline of the method used. 60 minutes is the time taken for surgery of n=12 pups. Recovery periods were undertaken in the dam. The interventions used were: sham animals, positive controls, 75% xenon (balance oxygen), 33° C. hypothermia, 20% xenon (25% oxygen, 55% nitrogen), 35° C. hypothermia, and a combination of 35° C. hypothermia and 20% xenon. Unless otherwise indicated, animals were kept at 37° C. and breathed a gas mixture of 25% oxygen balanced with nitrogen. Sham animals underwent incision, but no ligation or HI, and positive controls had both surgery and HI. Animals in each group were divided equally between the variable recovery periods (16, 24 and 48 h) before being sacrificed. Abbreviations: HI, hypoxia-ischamia.

Figure 11:
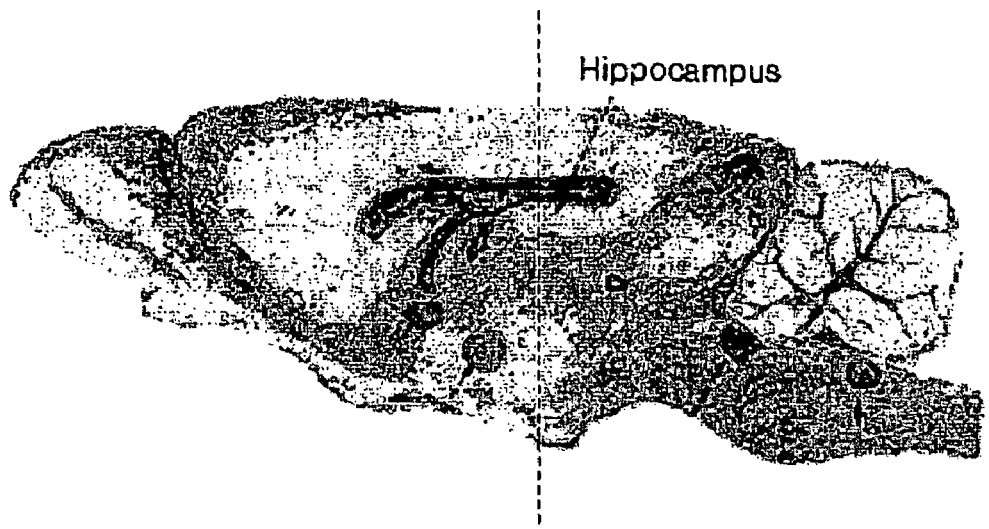
Figure 11:
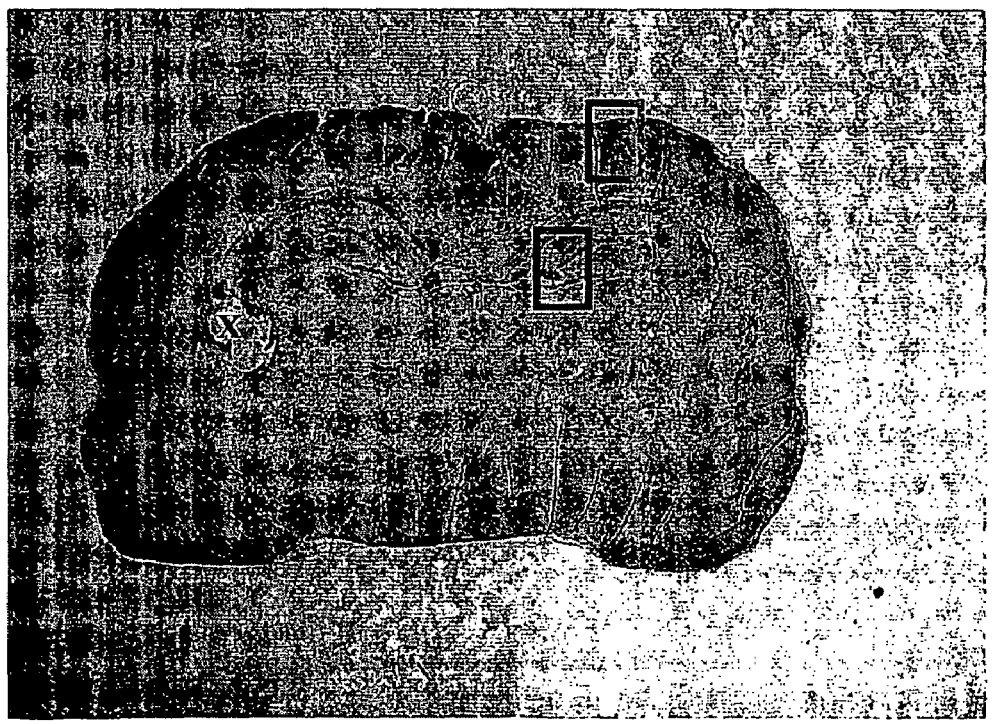

FIG. 11 shows (A) Sagittal section of a rat brain modified from website: faculty.virginia.edu/.../RatBrainLabels.jpg. The broken line represents the area of the brain from which coronal sections (B) were taken, approximately −3.6 mm from the bregma. (B) shows a cresyl violet-stained coronal section. The boxes indicate the areas in which the counting frames were placed and the cells were analysed—the top box indicates the cortex and the bottom one, the gyrus. X overlies a hole that was intentionally created with a safety pin in order to demonstrate the non-ligated (contra lateral) hemisphere.

Figure 12:
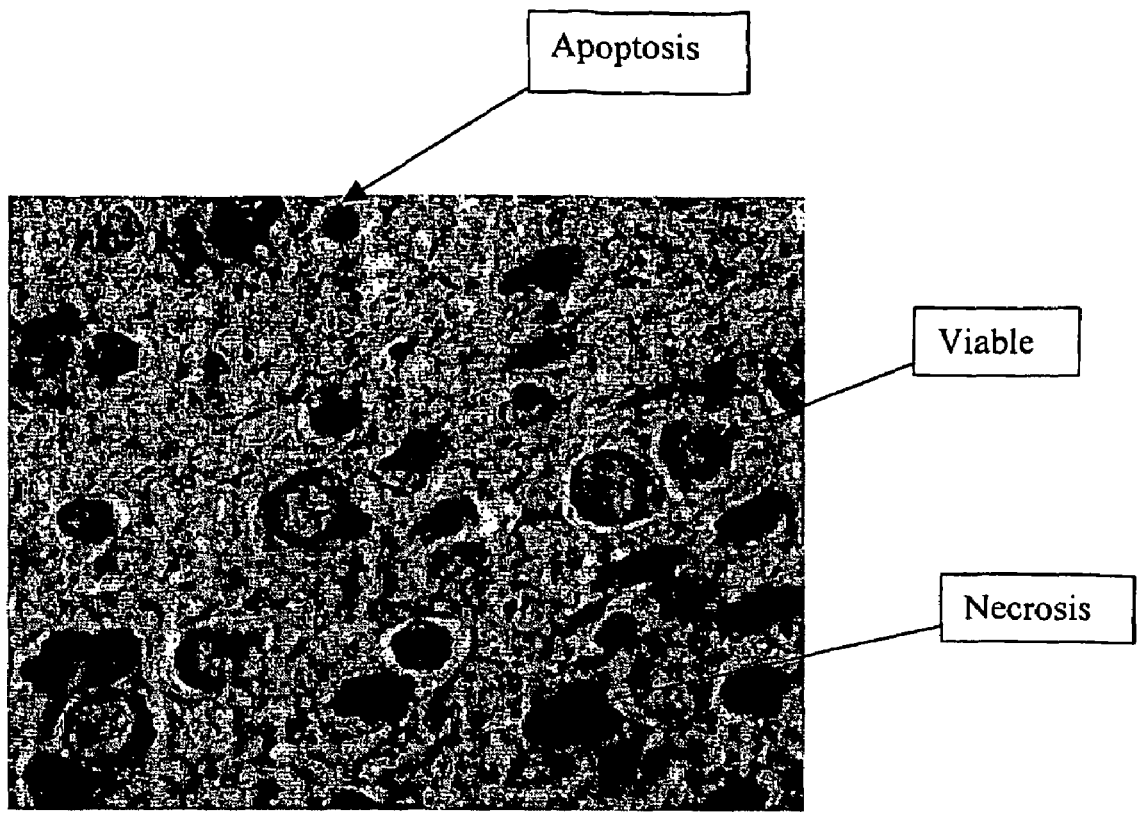

FIG. 12 shows a photomicrograph of the cortex (cresyl-violet stained), taken with a 100× oil emersion lens and an Axiocam digital camera, demonstrating the difference in morphological appearance between an apoptotic, necrotic and viable cell. Viable cells stain less intensely than either type of cell death and therefore have a paler cytoplasm, whereas dead cells are more darkly stained. Necrotic and apoptotic cells are differentiated on the basis of their different nuclear appearances—necrotic nuclei are large and irregularly shaped, whereas apoptotic nuclei are small, shrunken, and spherically shaped.

Figure 13:
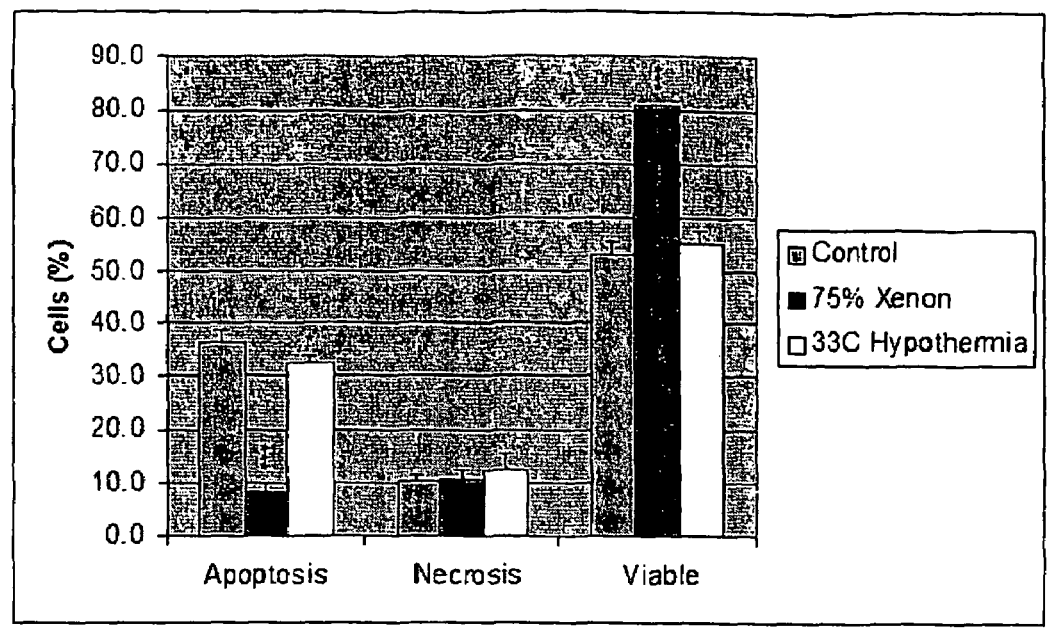
Figure 13:
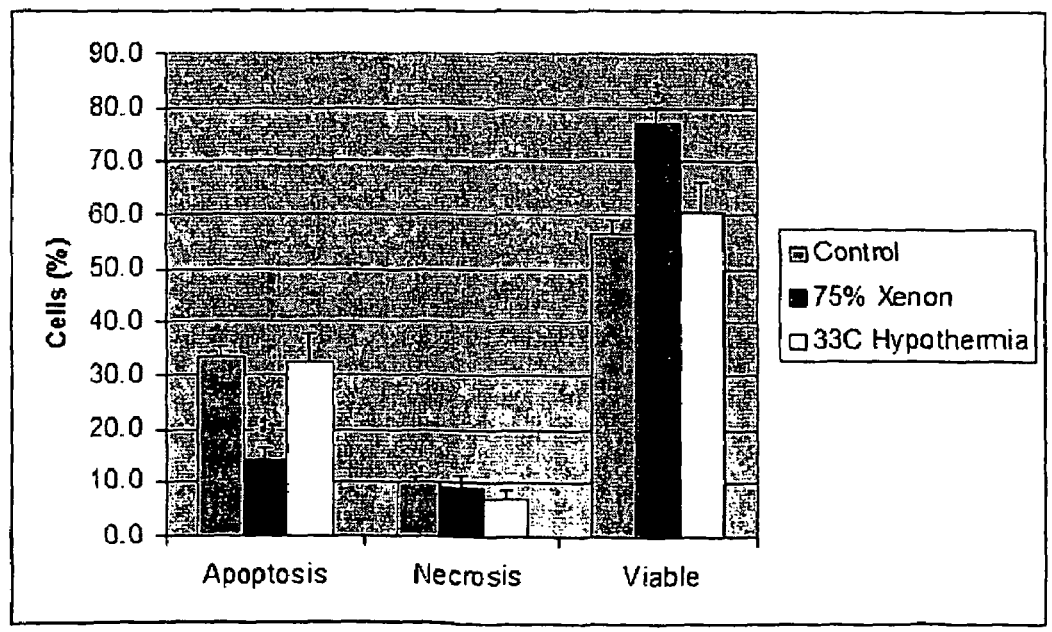

FIG. 13 shows that xenon is neuroprotective at 16 h via an anti-apoptotic mechanism. More specifically, FIG. 13 shows graphs for apoptotic and necrotic neuronal death induced by hypoxic-ischaemia, and the effects of 75% xenon and 33° C. hypothermia on such cell death at 16 h in (A) the cortex, and (B) the gyrus. In both brain areas xenon significantly increases the percentage of viable cells as well as decreasing the percentage of apoptotic cells compared to positive control animals. In the cortex, hypothermia decreases the percentage of apoptotic cells, although it does not increase the viable cell count and can therefore not be considered neuroprotective. Results are mean±SD (n=3). *$p<0.05$, $p<0.01$, *$p<0.001$ vs. positive controls.

Figure 14:
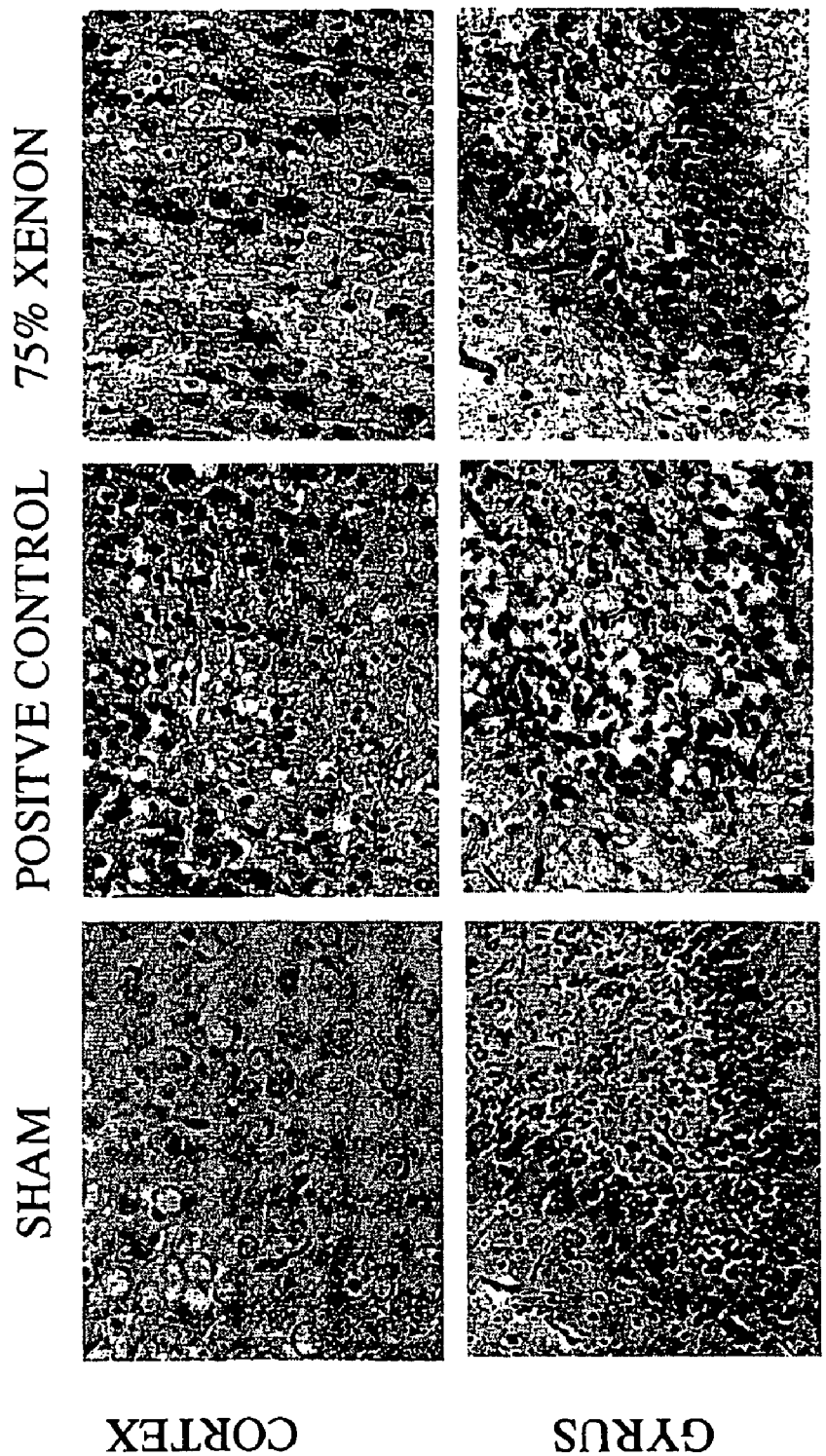

FIG. 14 shows a photomicrograph demonstrating the cortex and gyrus in the sham, positive control and 75% xenon animals at 16 hours. The 75% group is more similar in appearance to the sham group than the positive control group. This confirms the neuroprotective effect of xenon at 16 hours. The gyrus of the control group is distorted in shape due to the increased amount of cell death and vacuolation.

Figure 15:
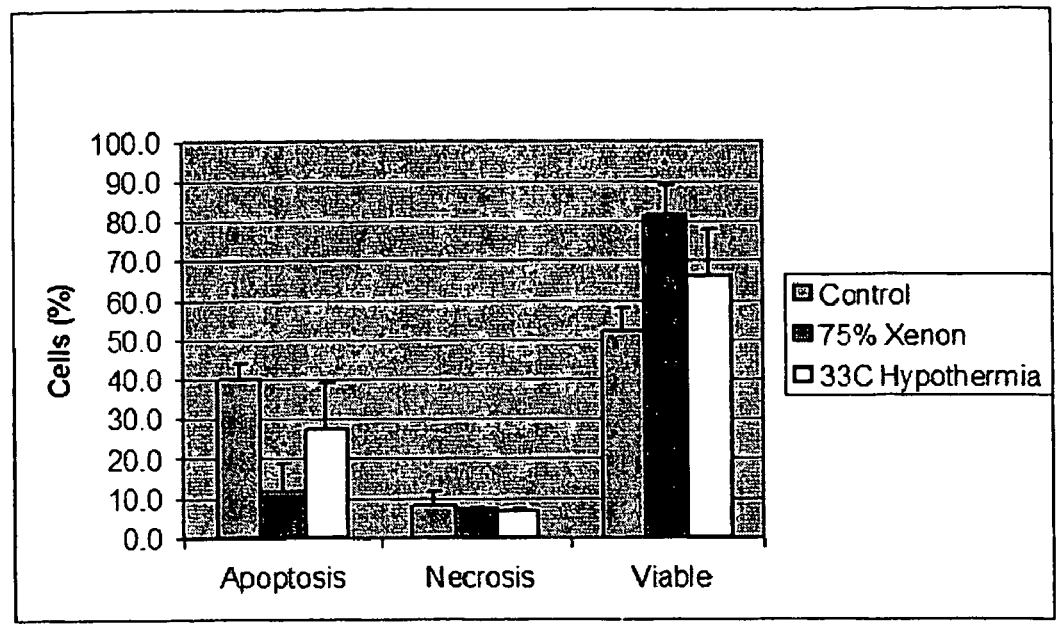
Figure 15:
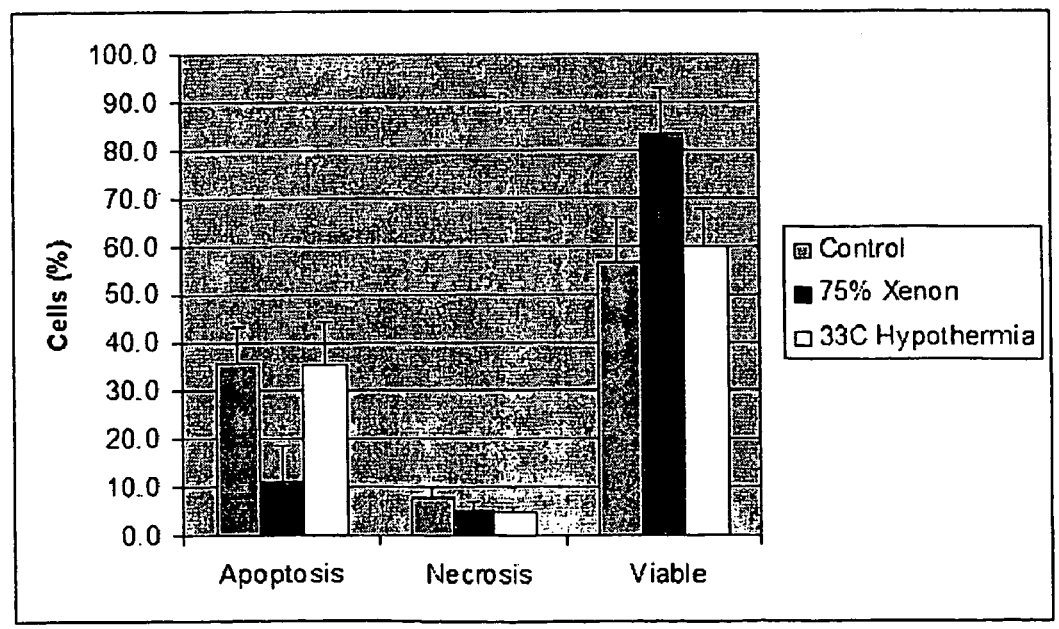

FIG. 15 shows that xenon is neuroprotective at 24 h via an anti-apoptotic mechanism. More specifically, FIG. 15 shows graphs for apoptotic and necrotic neuronal death induced by hypoxic-ischaemia, and the effects of 75% xenon and 33° C. hypothermia on such cell death at 24 h in (A) the cortex, and (B) the gyrus. In both brain areas xenon causes a significant increase in the percentage of viable cells due to a decreased necrotic cell count. Results are mean±SD (n=3). *$p<0.05$ vs. positive controls.

Figure 16:
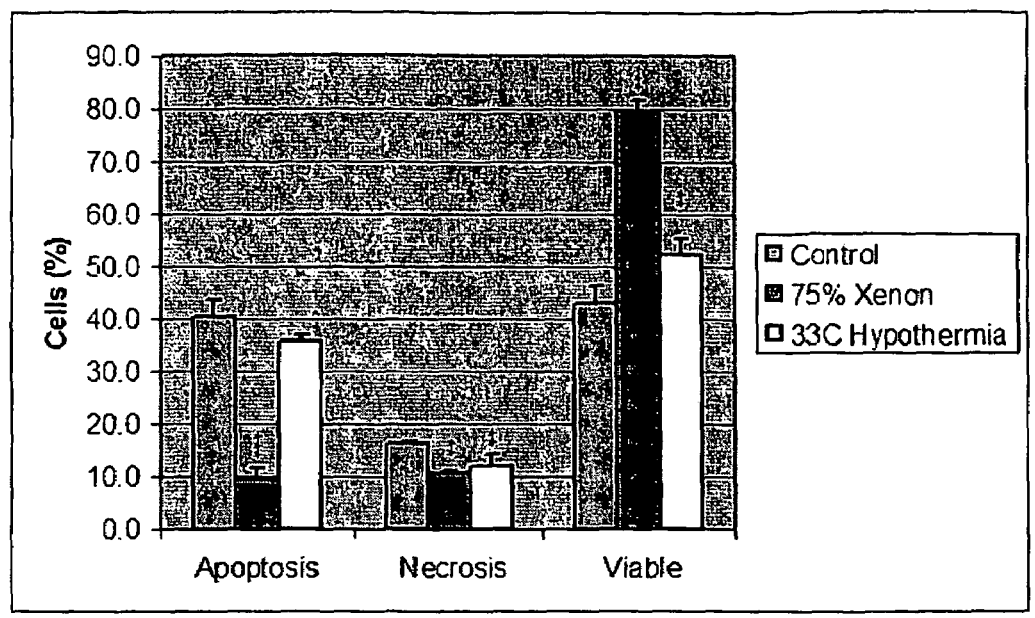
Figure 16:
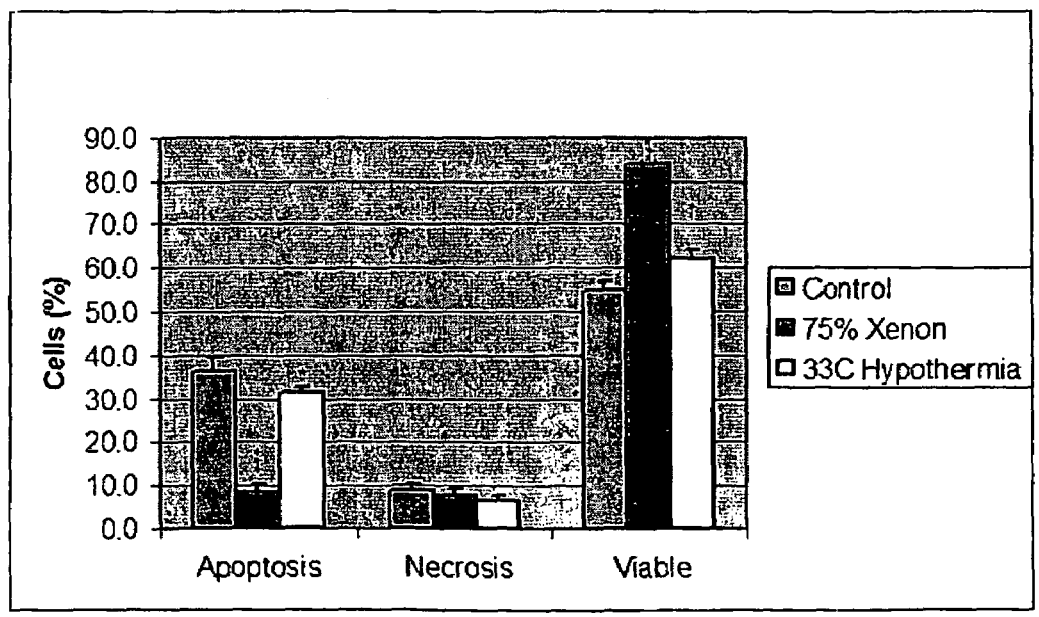

FIG. 16 shows that xenon is neuroprotective at 48 h via an anti-apoptotic mechanism More specifically, FIG. 16 shows graphs for apoptotic and necrotic neuronal death induced by hypoxic-ischaemia, and the effects of 75% xenon and 33° C. hypothermia on such cell death at 48 h in (A) the cortex, and (B) the gyrus. Xenon is neuroprotective via an anti-apoptotic mechanism in both the cortex and the gyrus. In addition, xenon has an anti-necrotic effect in the cortex. 33° C. hypothermia appears to be neuroprotective in both brain areas, but by a different mechanism—it is anti-necrotic in the cortex, and anti-apoptotic in the gyrus. Results are mean±SD (n=3). *$p<0.05$, $p<0.01$, *$p<0.001$ vs. positive controls.

Figure 17:
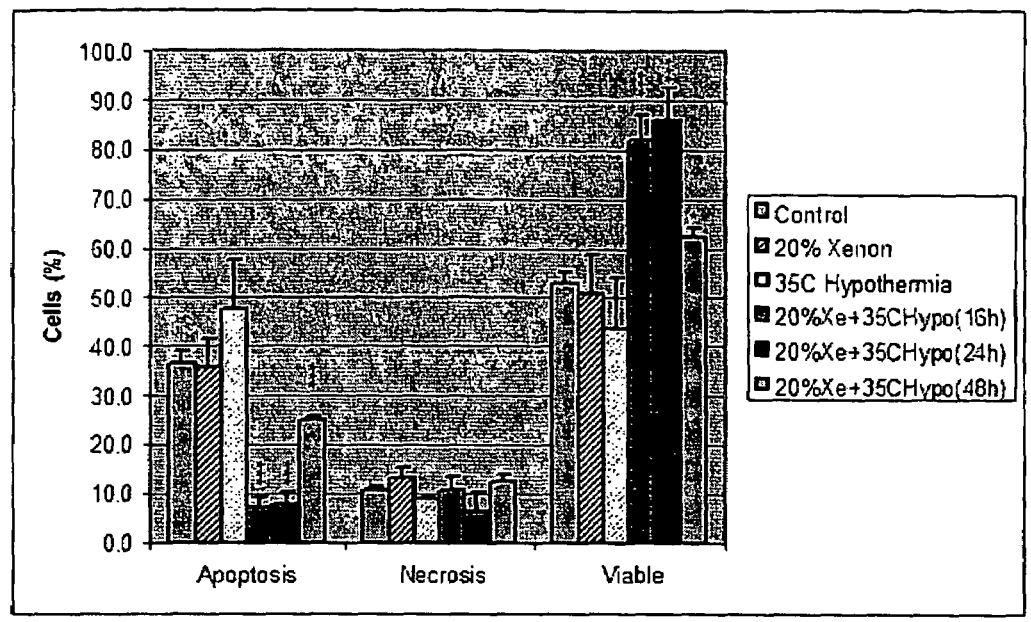
Figure 17:
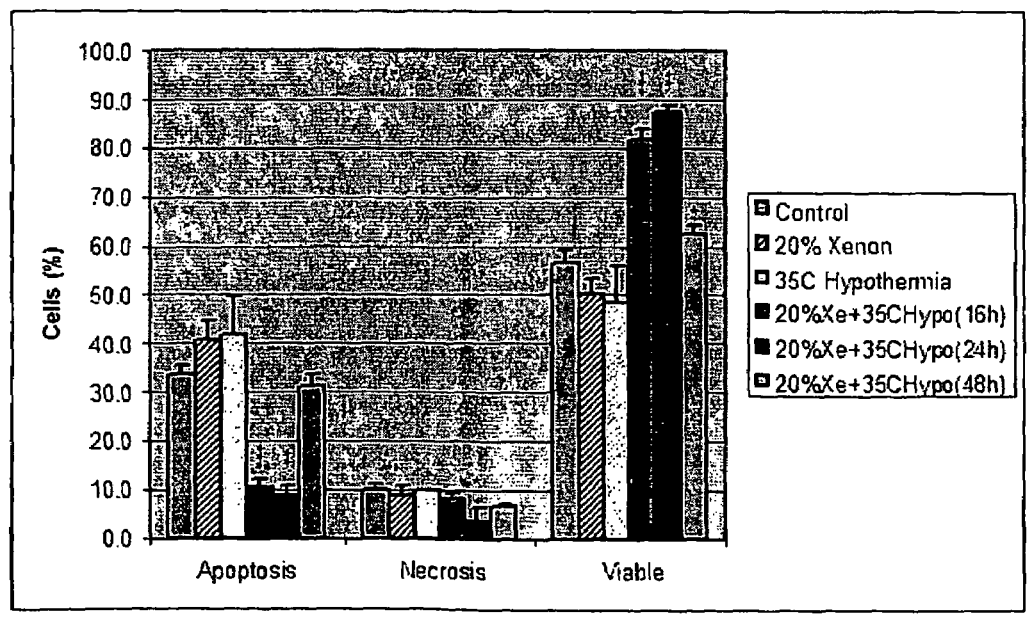

FIG. 17 shows that a combination of xenon and hypothermia interact synergistically to produce anti-apoptotic neuroprotection. More specifically, FIG. 17 shows graphs for apoptotic and necrotic neuronal death induced by hypoxic-ischaemia, and the effect of a combination of 20% xenon and 35° C. hypothermia on such cell death at 16, 24 and 48 h in (A) the cortex, and (B) the gyrus. No difference was seen when the 20% xenon group and the 35° C. hypothermia group were compared to positive controls, thus at these values there is no neuroprotection. When these values are used in combination however, there is a dramatic increase in the percentage of viable cells due to a significant decrease in the apoptotic cell count as compared to positive control animals. In the gyrus, the combination provides an additional anti-necrotic effect at 24 h. Results are mean±SD (n=3). *$p<0.05$, $p<0.01$, *$p<0.001$ vs. positive controls.

EXAMPLES

Example 1

Neonatal Asphyxia Model

Seven day old postnatal Sprague-Dawley rats underwent right common carotid artery ligation under surgical anaesthesia (1%-1.5% isoflurane in pure oxygen). After ligation, the animals were returned to their mothers and placed in a specially designed area with constant of room temperature (23° C.) and humidity (48%). One hour after surgery, neonatal rats were placed in specially designed chamber with 8% oxygen combined with 0, 20, 40, 60 or 70% Xenon (with nitrogen making up the balance) for 90 min at 37° C. (temperature kept by water bath running outside chambers). At post-experimental day 7, rats (14 day old) were killed and their brains removed. The ratio of right hemisphere weight against left (R/L ratio) was calculated. Rat pups in some groups were allowed to live up to 30 days of postnatal age, at which time their neuromotor function and co-ordination were assessed with established protocols (Neuromotor testing and Rotarod testing).

Figure 1:
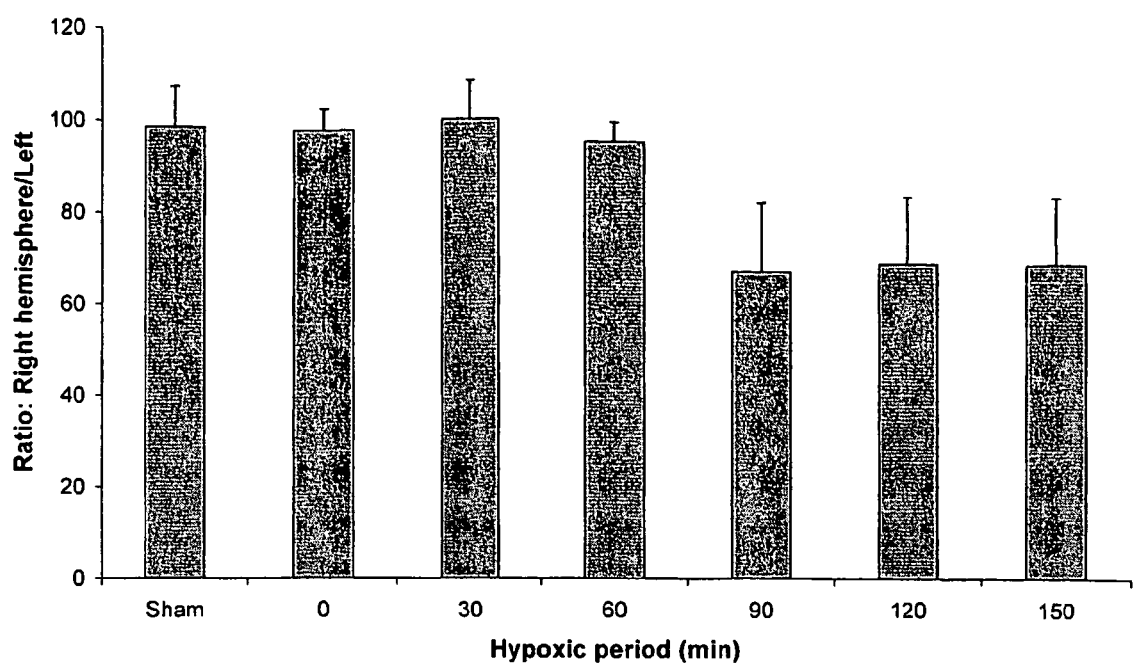
FIG. 1 shows the relationship between damage, as measured by loss of brain weight (ratio of right hemisphere/left) and the duration of the hypoxic period (in minutes) in Sprague-Dawley rats.

The results indicate that with increasing times of hypoxia, damage (as measured by loss of brain weight) is only evident when the hypoxia exceeds 90 minutes (FIG. 1). Hence, the standard period of hypoxic injury was set to be 90 minutes.

Figure 2:
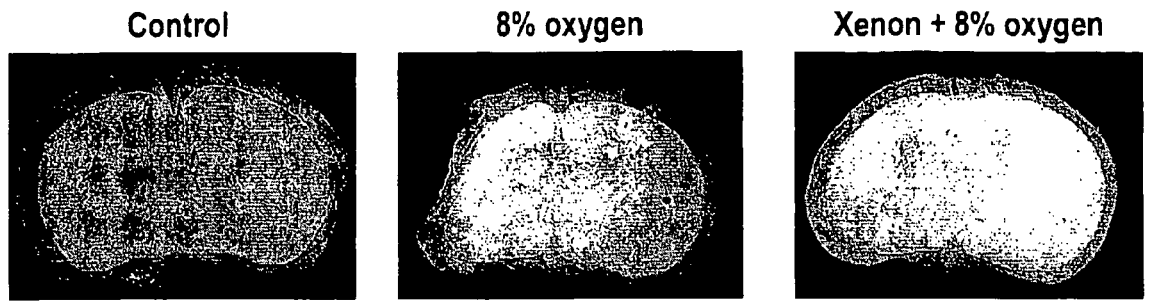
FIG. 2 shows brain sections from Sprague-Dawley rats that have suffered 90 minutes of hypoxia-ischemia injury.

Brain sections from animals that suffered 90 minutes of hypoxia-ischemia injury are shown in FIG. 2. In more detail, FIG. 2 (centre) show gross anatomical deterioration (on the side of the brain that sustained the injury—left side in this view) compared to control animals (left). The brain slices on the right are from animals that have suffered the same hypoxia-ischemia but have been breathing 70% xenon during the hypoxic period. These brains look close to normal showing the remarkable neuroprotection afforded by xenon.

Figure 3:
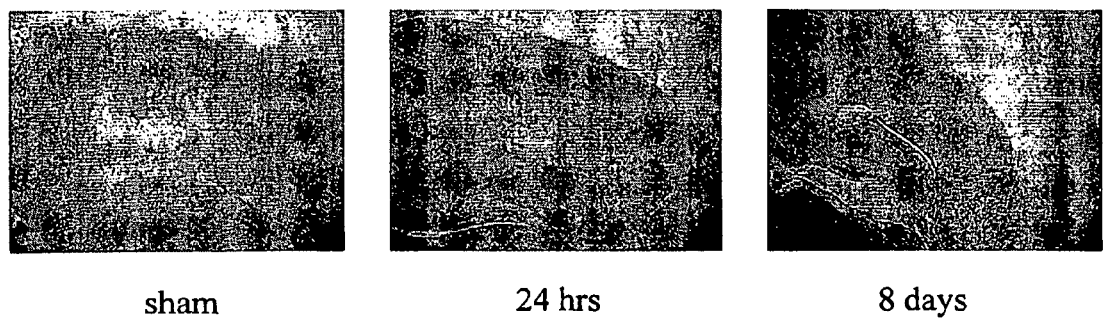
FIG. 3 shows the major cellular damage which is evident in Sprague-Dawley rats 24 hours after 90 minutes of hypoxia-ischemia.

The major cellular damage which is evident 24 hours after 90 minutes of hypoxia-ischemia is shown in FIG. 3.

Figure 4:
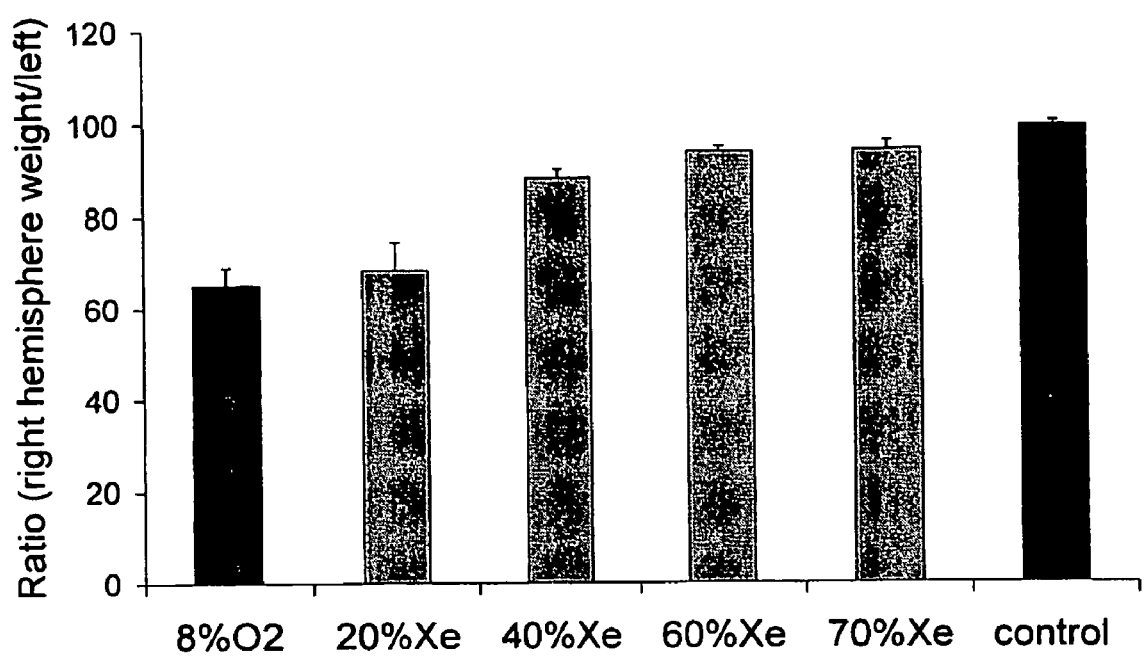
FIG. 4 shows the concentration-dependence of xenon neuroprotection (ratio right hemisphere weight/left against xenon concentration).

The concentration-dependence of xenon neuroprotection (ratio right hemisphere weight/left against xenon concentration) is shown in FIG. 4. In more detail, FIG. 4 shows the ratios of ipsilateral/contralateral hemispheric weight of 14 day rat brain after hypoxia/ischemia with or without various concentrations of xenon at 7 days old. Neuroprotection is evident even at sub-anaesthetic concentrations. Control animals were subjected to carotid ligation but no hypoxia was given. Results are mean±SEM (n=5-8). * P<0.01 vs 8% $O_2$.

Figure 5:
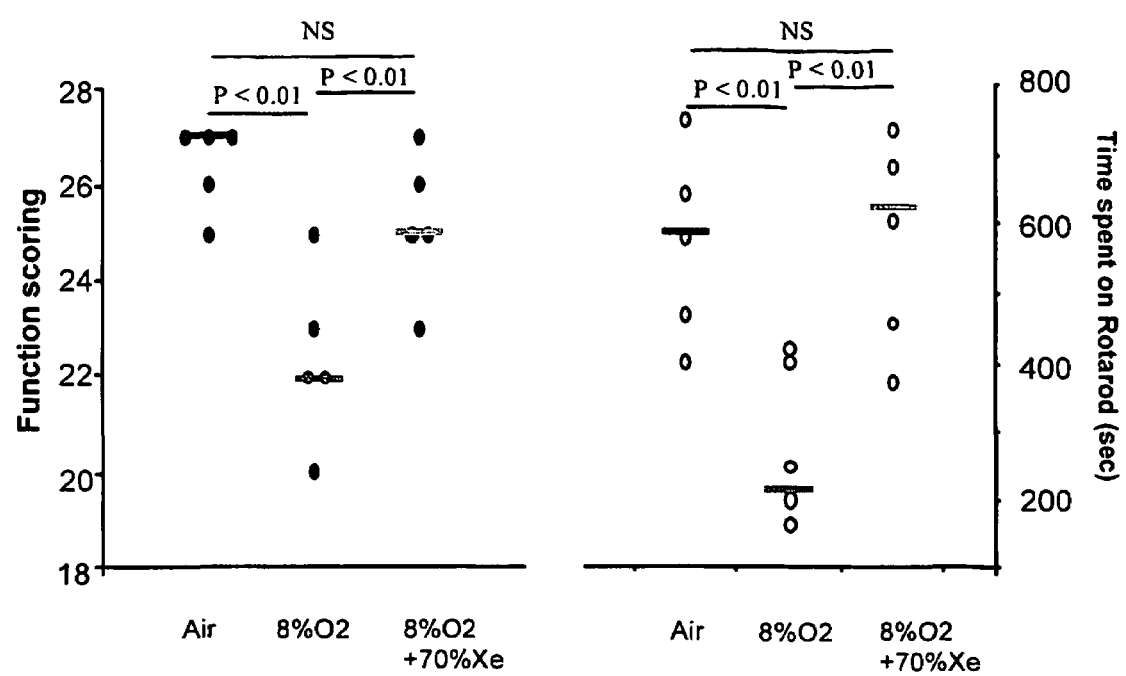
FIG. 5 shows the effect of 70% xenon on neurological functions assessed remotely after hypoxic-ischemic (HI) insult.

The effect of 70% xenon on neurological functions assessed remotely after hypoxic-ischemic (HI) insult is shown in FIG. 5. At postnatal day 7 the right carotid artery was ligated and rat pups were exposed to a hypoxic environment (8% oxygen+70% xe and balance with nitrogen) for 90 min. Thirty days after the insult, rats were evaluated for neuromotor function (A) using a panel that included assays of prehensile traction, strength, and balance beam performance (graded on a 0-9 scale) and (B) balance on a Rotarod, a standard test of balance and neuromotor function. The data point from an individual rat is the sum of three tests. The horizontal bars indicate the median for each group.

The neuroprotective effect (ratio of right hemisphere/left) observed with $N_2$ and xenon respectively is shown in FIG. 6, when xenon is administered 2 hours post HI insult. In more detail, the data show that xenon is effective in providing neuroprotection even if it is administered 2 hours after the end of the hypoxic period. The ratios of ipsilateral/contralateral hemispheric weight of 14 day rat brain after 90 min hypoxic-ischemia insult and then 2 hrs recovery following exposure with 70% $N_2$ or 70% Xe+30% $O_2$ for 90 min at 7 days old. Results are mean±SEM (n=6).

The effect of mild hypothermia on the neuroprotective effect of xenon (LDH release against xenon concentration, % atm) is shown in FIG. 7. Modest hypothermia produces a very large and unexpected enhancement in xenon neuroprotection. Cooling by 4 degrees greatly enhances the potency of xenon in blocking LDH release. In more detail, this figure shows the effect of a combination of xenon and hypothermia on oxygen-glucose deprivation (OGD)-induced lactate dehydrogenase (LDH) release. FIG. 7 shows the results of exposing neuronal cultures to 75 minutes OGD in the presence of increasing concentrations of xenon, either at 37° C. (red), or at 33° C. (blue). The $ED_{50}$ values for xenon at 37° C. vs xenon at 33° C. were 35.9+/-2.15% and 11.5+/-2.0% (means +/-SEM) respectively. Neuronal injury is expressed as a percentage of the maximal LDH release after 75 minutes of OGD and 6 hours of recovery in the absence of either xenon or hypothermia. Points represent mean values, with error bars indicating standard errors.

The extent of the temperature-dependence of the process is shown in FIG. 8 which shows a van't Hoff plot of the natural logarithm of LDH release plotted against reciprocal absolute temperature. From the slope of such a plot the enthalpy change of the process can be calculated, its size being a measure of the temperature dependence. The data in red show the effect of temperature on LDH release in the absence of xenon. The reduction of release as the temperature is reduced is expected but modest. When 12.5% xenon is present, the temperature dependence is very large and unexpected. Hypothermia therefore appears to greatly enhance the neuroprotective effects of xenon. Accordingly, the results suggest that hypothermia and xenon act synergistically as neuroprotectants.

More detailed studies are outlined below in Example 2.

Example 2

Materials & Methods

This study conformed to the United Kingdom Animals (Scientific Procedures) Act of 1986 and was approved by the Home Office (U.K.).

Animal Model of Hypoxia-Ischaemia

This study used a 7-day-old (p7) rat model of focal HI in which the pattern of brain injury resembled that of hypoxic-ischemic injury in the term human neonate (Johnston, 1983).

p7 Sprague-Dawley rat pups (weighing between 10 and 14 g) from Harlan, U.K. were subjected to a previously described model of HI injury (Levine, 1960; Rice et al, 1981). In brief, rat pups were anaesthetised with 2% isoflurane before undergoing permanent unilateral ligation of the right common carotid artery, using a midline neck incision and 5.0 silk suture. Once surgery was complete, pups recovered from the anaesthesia and were then returned to the dam until the time of experimentation.

1 hr after surgery, pups were exposed to hypoxia by placing them into purpose-built, airtight chambers that were partially submerged in a 37° C. water bath (FIG. 9). A hypoxic period of 90 minutes was chosen as preliminary experiments indicated that hypoxic-ischaemic damage, as measured by hemisphere weight, is maximal after this time. Hypoxia was induced by a continuous flow of humidified 8% oxygen, balanced with nitrogen, and this mixture was monitored every 15 minutes by a Datex Ohmeda (Bradford, U.K.). (All gases were supplied by BOC.)

Experimental Treatments

Following HI, pups were returned to the dam for 4 hrs to recover, after which time they were subjected to 90 minutes of one of the experimental interventions below. Data from preliminary experiments demonstrated that the optimum time at which to apply the intervention was either concurrently with HI or 4 h afterwards. No significant difference existed between the two time periods and thus 4 h post-insult was chosen as the time to apply the intervention, as it was thought to be the most clinically relevant.

Pups were returned to their mothers until sacrifice at 16, 24 and 48 h following treatment (Northington et al, 2001) (FIG. 10).

Controls

Control groups consisted of (a) non-treated littermates that underwent incision but no ligation (i.e. sham animals), used as negative controls, and (b) littermates exposed to HI, but not to the experimental intervention, to act as positive controls. These animals were subjected to 90 minutes at 37° C. and a gas mixture composed of 25% oxygen and balanced nitrogen.

Experimental Rats

Following HI and recovery, experimental rats were treated with 90 minutes of one of the five experimental interventions below. Each of the five treatments was carried out on separate groups of rats.

Treatment with Hypothermia

Rat pups underwent 90 minutes of treatment with mild hypothermia (33° C.). One pup was selected at random, and under isoflurane and local anaesthesia, a temperature probe (Mini-Mitter Co. Inc., Bend, Oreg., U.S.A.) was inserted into the cortex and held in place with superglue. All pups were then placed into the airtight chambers (as before), and a mixture of 25% oxygen and balanced nitrogen was pumped through. The chambers were partially submerged in a water bath that was maintained so as to keep the cortical temperature of the pups at exactly 33° C., as measured by the temperature probe and Vital View computer software. This temperature was chosen as it represents "mild" hypothermia, and was thus thought to be clinically relevant, providing a good balance between side effects and benefit. After 90 minutes of treatment, the pups recovered with their mother until the time of sacrifice. The pup with the temperature probe in place was culled immediately after the experiment, and its brain was not used for analysis.

Treatment with Xenon

The same experimental paradigm was followed for treatment with xenon, but instead of hypothermia, the water bath was maintained at 37° C. and the gas mixture was changed to 25% oxygen and 75% xenon for 90 minutes. Gas was delivered into a purpose-built, closed system to minimise xenon leakage (FIG. 9). Once again, the pups were returned to their mothers until sacrifice.

Combination Protocol

In the combination paradigm, the rats underwent both hypothermia and xenon concurrently for 90 minutes. Again, the pups were placed in airtight chambers, but on this occasion, their temperatures were maintained at 35° C. and the gas mixture consisted of 25% oxygen, only 20% xenon and balanced nitrogen. This temperature and xenon concentration was shown in preliminary experiments, to confer no neuroprotective benefit to the developing brain when used independently. Thus, by using these values, any neuroprotective benefit at all is indicative of synergy between the two agents. Following treatment, pups were returned to their mothers until sacrifice.

In order to demonstrate that the values used in the combination group conferred no neuroprotection when used independently, two more groups of experimental rats were used: one group underwent hypothermia (as before) at 35° C., and the other group was exposed to xenon at a concentration of 20%.

Tissue Preparation

Brain Harvesting

Brains were retrieved at 16, 24 and 48 h following the end of the experimental protocol.

Animals were killed with an overdose of pentobarbital (100 mg/kg) intraperitoneally, and then exsanguinated with 2.5 u/ml heparin in PBS via transcardial perfusion through the left ventricle. This was followed by perfusion with 20 ml 4% paraformaldehyde in PBS and subsequent brain removal. Brains were then post-fixed overnight in the same fixative. For each time group, the number of control, or experimental brains was divided equally and either sliced as frozen sections for immunohistochemistry, or embedded in paraffin for histological analysis. In order to distinguish between the ipsilateral and contra lateral hemispheres, a paperclip was used to make a hole in the contra lateral, unaffected (left) hemisphere before slicing.

Paraffin Embedding

After post-fixing, brains for histology were dehydrated using a Histokinette 2000 tissue-embedding processor (Leica U.K. Ltd., Milton Keynes, U.K.) and then embedded in paraffin wax blocks. The paraffin-embedded brains were cut in coronal sections at a thickness of 5 μm using a microtome (Leica, Germany). FIG. 10.3 illustrates the area of the brain from which the slices were taken. Approximately 20 slices were taken from each brain in the region of the hippocampus, (as this is the area most vulnerable to HI injury) around −3.6 mm from the bregma.

Frozen Sections

Once the brains had been post-fixed overnight, they were cryoprotected in 30% sucrose in PBS (this also contained 2 mg/ml sodium azide) and stored in the fridge for 48 h, or until they had sunk to the bottom of the tube. The brains were then frozen in O.C.T. compound (BDH, Poole, England) at −22° C. and coronal sections were cut at 30 μm on a sliding cryostat (Bright Instrument Company Ltd., Huntingdon, U.K.). Sliced brains were stored in the fridge in wells containing 0.1 M PBS and 1 mg/ml sodium azide, before being stained for immunohistochemistry (see below).

Staining Procedures

Histology

Paraffin-embedded sections were mounted on slides and stained with cresyl violet for histology as described previously (Wilhelm et al, 2002).

Neuropathological Analysis of Necrosis and Apoptosis

Histology Microscopy

Neuronal injury was assessed by histological analysis of paraffin brain slices stained with cresyl violet. Cresyl violet is a basic stain that binds to acidic components of neuronal cytoplasm such as RNA-rich ribosomes, and also the nuclei and nucleoli of nerve cells. This technique was used to assess cell viability and whether non-viable cells exhibited apoptosis or necrosis on the basis of validated morphological criteria (Nakajima et al, 2000).

Each experimental group consisted of three time groups (16, 24, 48 h), and each time group contained three animals, (thus there were nine animals in total for each experimental group). Three slides per animal were chosen from the area of the brain that was −3.6 mm from the bregma (FIG. 11). Slides were then sorted into time groups and the examiner was blinded to the intervention.

Two areas from the ipsilateral side of each brain were analysed using a BX60 light microscope (Olympus, Southall, U.K.)—one in the cortex and one in the gyrus of the hippocampus (FIG. 11). A 40× objective lens with a grid was used to count the total number of cells that appeared in the grid. Cells were scored as either viable, apoptotic, or necrotic based on their morphological appearance, and the percentage of each cell type was noted down for each of the brain areas. An Axiocam digital camera (Zeiss, Göttingen, Germany) was used along with the microscope to take photomicrographs of the brain slices.

The criteria for assigning cells to each category was as follows (FIG. 12):

1. Cells undergoing either type of cell death (apoptosis or necrosis) took up the cresyl violet stain more intensely than viable cells, which were regularly shaped with pale cytoplasm, and a clearly visible, darker nucleus.
2. Cells classed as apoptotic had very darkly stained, shrunken nuclei that were spherically shaped, and an intact cell membrane, often with a surrounding area of vacuolation.
3. Necrotic cells on the other hand, though also very intensely stained, had very irregularly shaped, enlarged nuclei.

The number of apoptotic, necrotic and viable cells was expressed as a percentage of the total cell number and noted down for each slide. A mean percentage was then calculated for each animal from the three slides, so that each of the three animals in a time group had only one value. A further mean was taken from these three animals in order to obtain only one value for each time group, and the standard deviation was recorded.

Statistical Analysis

Data analysis was performed using one-way ANOVA followed by Student-Newman-Keuls where appropriate. A $p<0.05$ was considered to be statistically significant.

Results

Xenon and Hypothermia as Independent Agents

Xenon is Neuroprotective in the Neonate by an Anti-Apoptotic Mechanism

Microscopic analysis of cortical and hippocampal brain regions demonstrated the neuroprotective properties of xenon, by the similar morphological appearance of xenon-treated brains as compared to sham brains, and the difference in appearance when compared to brains from rats that were not treated with xenon (FIG. 14). Profound neuroprotection against hypoxic-ischaemic injury in the neonatal rat was achieved by the use of xenon at its maximal concentration (75%), and this was quantified by histological analysis of brain slices stained with cresyl violet. The independent use of this concentration of xenon significantly decreased apoptotic cell death and increased the viable cell count. At 16 h, apoptosis in the cortex was reduced from 36.5%±2.5% in positive controls, to 8.5%±1.6% ($p<0.001$), and the viable cell count was increased from 52.9%±2.3% in positive controls, to 80.6%±0.2% ($p<0.001$) (FIG. 13A). In the gyrus, apoptosis was decreased from 33.6%±1.8% in positive controls, to 13.9%±2.4% ($p<0.01$), and the viable cell count was raised from 56.5%±2.6% in positive controls, to 77.1%±3.3% ($p<0.01$) (FIG. 13B). The 24 and 48 h groups (FIGS. 15 and 16 respectively), showed similar results to the 16 h group, with xenon exhibiting statistically significant anti-apoptosis when compared to the positive control animals, in both the cortex and the gyrus.

Anti-necrosis by xenon was shown to be statistically significant in the cortex at 48 h, where it decreased necrosis from 16.6%±0.2% in positive controls, to 10.7%±0.4% ($p<0.01$) (FIG. 16A). Xenon was not however anti-necrotic in the gyrus at 48 h (FIG. 16B). At all other time groups (16 and 24 h) xenon was not anti-necrotic.

90 Minutes of 33° c. Hypothermia after moderate HI is Ineffective

No neuroprotection was observed with 33° C. hypothermia at 16 or 24 h (FIGS. 13 and 15 respectively). At 16 h, hypothermia appeared to have a significant anti-apoptotic effect in the cortex, but as the viable cell count was not statistically different to the positive control animals, it can be concluded that this intervention provided no neuroprotection. At 48 h however, hypothermia was neuroprotective via an anti-necrotic mechanism in the cortex, reducing the necrotic cell count from 16.6%±0.2% in the positive controls, to 12%±2.3%, and increasing the viable cell count from 43%±3.4% to 52.3%±3.1% (FIG. 16A). In the gyrus at 48 h, hypothermia provided neuroprotection in an anti-apoptotic manner (FIG. 16B).

Xenon and Hypothermia in Combination

Treatment with 20% Xenon Alone Shows No Neuroprotection

Contrary to the results obtained with 75% xenon, 20% xenon exerts no neuroprotective effect. By looking at FIG. 17, it can be seen that the percentage of apoptosis found in the cortex of the 20% xenon group at 16 h, is 36%±5.7% compared with 37%±2.5% in the positive control animals ($p>0.05$) and the percentage of viability is 51%±7.8% compared to 53%±2.3% respectively ($p>0.05$), (i.e. there is no statistical difference between 20% and positive control groups). The data from the gyrus produced very similar results.

Treatment with 35° C. Hypothermia Alone Shows No Neuroprotection

35° C. hypothermia used alone is ineffective against HI, and shows no statistical difference in either brain area when compared to positive controls. The percentage of apoptosis is 48%±10.1% versus 37%±2.5% in positive controls, and percentage cell viability is 44%±10.3% versus 53%±2.3%.

Treatment with a combination of 20% xenon+35° C. hypothermia demonstrates synergistic neuroprotection via an anti-apoptotic mechanism. By using proven ineffective interventions of either xenon (20%) or hypothermia (35° C.) in combination, a profound synergistic neuroprotection was demonstrated in both areas of the brain, and across all three of the time groups (16, 24 and 48 h) via an anti-apoptotic mechanism.

Post-ischaemic application of the combination treatment significantly reduced the degree of apoptotic cell death, and increased the proportion of viable cells (see FIG. 17). At 16 h in the cortex, the reduction of apoptosis due to the combination therapy, was found to be from 35.8%±5.7% and 47.6%±10.1% in the 20% xenon and 35° C. hypothermia groups respectively, to only 7.2%±2% in the combination group (p<0.01 and p<0.001 respectively), while the viable cells were increased from 51%±7.8% and 43.7%±10.3%, to 82.3%±4.9% (p<0.01 in both groups). Data from the gyrus produced similar results (FIG. 17B) apart from the 24 h group, which appeared to provide anti-necrotic as well as anti-apoptotic protection Considering the fact that no neuroprotection was provided by the individual agents, the results of the combination are astounding, and certainly far superior than had been anticipated. The level of neuroprotection provided by the combination of two individually ineffective interventions, demonstrates that synergy exists in vivo between xenon and hypothermia.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in the relevant fields are intended to be within the scope of the following claims.

REFERENCES

Albers, G., Goldberg, M. P., Choi, D. W., 1989. N-methyl-D-aspartate antagonists: ready for clinical trial in brain ischemia? Ann Neurol 25:398-403.

Ankarcrona, M., 1995. Glutamate-induced neuronal death: A succession of necrosis or apoptosis depending on mitochondrial function. Neuron 15:961-973.

Arias, R. L., Tasse, J. R. P., Bowlby, M. R., 1999. Neuroprotective interaction effects of NMDA and AMPA receptor antagonists in an in vitro model of cerebral ischemia. Brain Research 816:299-308.

Balduini, W., De Angelis, V., Mazzoni, E., Cimino, M., 2000. Long-lasting behavioural alterations following a hypoxic/ischemic brain injury in neonatal rats. Brain Research 859: 318-325.

Bliss, T. V. P., Collingridge, G. L., 1993. A synaptic model of memory: long-term potentiation in the hippocampus. Nature 361:31-38.

Bosley, T. M., Woodhams, P. L., Gordon, R. D., Belazs, R., 1983. Effects of anoxia on the stimulated release of amino acid neurotransmitters in the cerebellum in vitro. J. Neurochem 40:189-201.

Busto, R., Dietrich, W. D., Globus, M. Y. T., 1987. Small differences in intraischemic brain temperature critically determine the extent of ischemic neuronal injury. Blood Flow Metab 7:729-738.

Choi, D. W., Koh, J-Y., Peters, S., 1988. Pharmacology of glutamate neurotoxicity in cortical cell culture: attenuation by NMDA antagonists. J. Neurosci 8:185-196.

Choi, D. W., Rothman, S. M., 1990. The role of glutamate neurotoxicity in hypoxic-ischemic neuronal death. Annu Rev Neurosci 13:171-182.

Chopp, M., Knight, R., Tidwell, C. D., Helpern, J. A., Brown, E., Welch, K. M., 1989. The metabolic effects of mild hypothermia on global cerebral ischemia and recirculation in the cat: comparison to normothermia and hypothermia. J Cereb Blood Flow Metab 9:141-148.

Chow, A., Ma, D., Hossain, M., Franks, N. P., Maze, M., 2003. Combined neuroprotection by xenon and hypothermia. Society Neuroscience Abstract 893(1).

Clancy, B., Darlington, R. B., Finlay, B. L., 2001. Translating developmental time across mammalian species. Neurosci 105(1):7-17.

Cullen, S. C., Gross, E. G., 1951. The anaesthetic properties of xenon in animals and human beings, with additional observations on krypton. Science 113:580-581.

Debillon, T., Daoud, P., Durand, P., Cantagrel, S., Jouvet, P., Saizou, C., Zupan, V., 2003. Whole-body cooling after perinatal asphyxia: a pilot study in term neonates. Developmental Medicine and Child Neurology 45:17-23.

Dingledine, R., McBain, C. J., 1999. Glutamate and aspartate in: Siegel, S. J., Agranoff, B. W., Albers, R. W., Fisher, S. K., Uhler, M. D., (Eds), Basic neurochemistry: Molecular, cellular and medical aspects, $6^{th}$ edition, Lippincott-Raven, pp 316-333.

Eilers, H., Bickler, P. E., 1996. Hypothermia and Isoflurane similarly inhibit glutamate release evoked by chemical anoxia in rat cortical brain slices. Anesthesiology 85:600-607.

Engelhard, K., Werner, C., Eberspäicher, E., Bachl, M., Blobner, M., Eberhard, H., Hutzler, P., Eberhard, K., 2003. The effect of the $\alpha_2$-agonist dexmedetomidine and the N-methyl-D-aspartate antagonist S(+)-ketamine on the expression of apoptosis-regulating proteins after incomplete cerebral ischemia and reperfusion in rats. Anesth Analg 96:524-531.

Erecinska, M., Nelson, D., Wilson, F., Silver, I. A., 1984. Neurotransmitter amino acid levels in rat brain during ischemia and reperfusion. Brain Research 304:9-22.

Franks, N. P., Dickinson, R., de Sousa, S. L. M., Hall, A. C., Lieb, W. R., 1998. How does xenon produce anaesthesia? Nature 396(6709):324.

Goto, T., Nakata, Y., Morita, S., 2003. Will xenon be a stranger or a friend? Anesthesiology 98:1-2.

Goto, T., Saito, H., Nakata, Y., Uezono, S., Ichinose, F., Morita, S., 1997. Emergence times from xenon anaesthesia are: independent of the duration of anaesthesia. British Journal of Anaesthesia 79:595-599.

Graham, S. H., Shiraishi, K., Panter, S. S., Simon, E. P., Faden, A. I., 1990. Changes in extracellular amino acid neurotransmitters produced by focal cerebral ischemia. Neurosci Lett 110:124-130.

Gunn et al, 2000. Curr Opin Pediatr. April; 12(2):111-5.

Gwag, B. J., Koh, J. Y., Demaro, J. A., Ying, H. S., Jacquin, M., Choi, D. W., 1997. Slowly triggered excitotoxicity occurs by necrosis in cortical cultures. Neurosci 77:393-401.

Hardingham, G. E., Bading, H., 2003. The yin and yang of NMDA receptor signalling. Trends in Neuroscience 26(2): 81-89.

Hauptman, M., Nelson, D., Wilson, D. F., Erecinska, M., 1984. Some changes in amino acid levels in rat brain synaptosomes during and after in vitro anoxia and simulated ischemia. Brain Research 304:23-35.

Hill, I. E., MacManus, J. P., Rasquinha, I., Tuor, U. I., 1995. DNA fragmentation indicative of apoptosis following unilateral cerebral hypoxia-ischemia in the neonatal rat. Brain Res 676:398-403.

Homi, H. M., Yokoo, N., Ma, D., Warner, D. S., Franks, N. P., Maze, M., Grocott, H. P., 2003. The neuroprotective effect of xenon administration during transient middle cerebral artery occlusion in mice. Anesthesiology 99:876-881.

Ikeda, M., Nakazawa, T., Abe, K., Kaneko, T., Yamatsu, K., 1989. Extracellular accumulation of glutamate in the hippocampus induced by ischemia is not calcium dependent in vitro and in vivo evidence. Neurosci Lett 96:202-206.

Ikonomidou, C., Bittigau, P., Koch, C., Genz, K., Hoerster, F., Felderhoff-Mueser, U., Tenkova, T., Dikranian, K., Olney, J. W., 2001. Neurotransmitters and apoptosis in the developing brain. Biochemical Pharmacology 62:401-405.

Ikonomidou, C., Mosinger, J. L., Olney, J. W., 1989. Hypothermia enhances protective effect of MK-801 against hypoxic/ischemic brain damage in infant rats. Brain Research 487:184-187.

Ikonomidou, C., Mosinger, J. L., Salles, K. S., 1989. Sensitivity of the developing rat brain to hypobaric/ischemic damage parallels sensitivity to N-methyl-D-aspartate neurotoxicity. J Neurosci 9:2809.

Ikonomidou, C., Price, M. T., Mosinger, J. L., 1989. Hypobaric-ischemic conditions produce glutamate-like cytopathology in infant rat brain. J Neurosci 9:1693.

Jevtovic-Todorovic, V., Olney, J. W., 2003. Neuroprotective agents in: Evers, A. S., Maze, M., (Eds), Anesthetic Pharmacology: Physiological principles and clinical practice, Churchill Livingstone, pp 557-572.

Johnston, M. V., 1983. Neurotransmitter alterations in a model of perinatal hypoxic-ischemic brain injury. Ann Neurol 13:511-518.

Katja, C. Z., Green, D. R., 2001. How cells die: Apoptosis pathways. J Allergy Clin Immunol 108(4):S99-S103.

Kauppinen, R. A., McMahon, H., Nicholls, D. G., 1988. $Ca^{2+}$-dependent and $Ca^{2+}$-independent glutamate release, energy status and cytosolic free $Ca^{2+}$-concentration in isolated nerve terminals following in vitro hypoglycaemia and anoxia. Neuroscience 27:175-182.

Komuro, R. P., 1993. Modulation of neuronal migration by NMDA receptors. Science 260:95.

Krystal, J. H., Karper, L. P., Seibyl, J. P., Freeman, R., Delaney, R., Bremner, J. D., Heninger, G. R., Bowers, M. B., Charney, D. S., 1994. Subanaesthetic effects of the non-competitive NMDA antagonist, ketamine, in humans: psychotomimetic, perceptual, cognitive and neuroendocrine responses. Arch Gen Psychiatry 51:199-214.

Kudo, M., Aono, M., Lee, Y., Massey, G., Pearlstein, R. D., Warner, D. S., 2001. Effects of volatile anesthetics on N-methyl-D-aspartate excitotoxicity in primary rat neuronal-glial cultures. Anesthesiology 95:756-765.

Leist, M., Nicotera, P., 1998. Apoptosis, excitotoxicity, and neuropathology. Experimental Cell Research 239:183-201.

Levine, S., 1960. Anoxic-ischemic encephalopathy in rats. Am J Pathol 36:1-17.

Low, J. A., 1993. The relationship of asphyxia in the mature fetus to long-term neurologic function. Clinical Obstetrics and Gynaecology 36(1):82-90.

Ma, D., Wilhelm, S., Maze, M., Franks, N. P., 2002. Neuroprotective and neurotoxic properties of the 'inert' gas, xenon. British Journal of Anaesthesia 89:739-746.

MacDonald, J. F., Schneiderman, J. H., Miljkovic, Z., 1986. Excitatory amino acids and regenerative activity in cultured neurons. Adv Exp Med Biol 203:425.

Mehmet, H., 2000. Caspases find a new place to hide. Nature 403:29-30.

Muir, K. W., Lees, K. R., 1995. Clinical experience with excitatory amino acid antagonist drugs. Stroke 26:503-513.

Nakajima, W., Ishida, A., Lange, M. S., Gabrielson, K. L., Wilson, M. A., Martin, L. J., Blue, M. E., Johnston, M. V., 2000. Apoptosis has a prolonged role in the neurodegeneration after hypoxic ischemia in the newborn rat. J Neurosci 20(2):7994-8004.

Nakata, Y., Goto, T., Morito, S., 2001. Clinical pharmacology of xenon. Int Anesthiol Clin 39:63-75.

Nicholls, D. G., Budd, S. L., 2000. Mithochondria and neuronal survival. Physiol Rev 80:315-360.

Northington, F. J., Ferriero, D. M., Graham, E. M., Traystman, R. J., Martin, L. J., 2001. Early neurodegeneration after hypoxia-ischemia in neonatal rat is necrosis while delayed neuronal death is apoptosis. Neurobiology of Disease 8:207-219.

Olney, J. W., 2003. Excitotoxicity, apoptosis and neuropsychiatric disorders. Current Opinion in Pharmacology 3:101-109.

Olney, J. W., Labruyere, J., Wang, G., Wozniak, D. F., Price, M. T., Sesma, M. A., 1991. NMDA antagonist neurotoxicity: mechanism and prevention. Science 254:1515-1518.

Onitsuka, M., Satoshi, M., Inokuchi, H., Shigemori, M., Higashi, H., 1998. Mild hypothermia protects rat hippocarnpal CA1 neurons from irreversible membrane dysfunction induced by experimental ischemia. Neuroscience Research 30:1-6.

Pellegrino-Giampietro, D. E., Cherici, G., Alesiana, M., Carla, V., Moroni, F., 1990. Excitatory amino acid release and free radical formation may cooperate in the genesis of ischemia-induced damage. J. Neurosci 10:1035-1041.

Perlman, J. M., 1999. Markers of asphyxia and neonatal brain injury. NEJM 341 (5):364-365.

Petzelt, C., Blom, P., Schmehl, W., Müller, J., Kox, W. J., 2003. Prevention of neurotoxicity in hypoxic cortical neurons by the noble gas xenon. Life Sciences 72:1909-1918.

Pohl, D., Bittigau, P., Ishimaru, M. J., 1999. N-methyl-D-aspartate antagonists and apoptotic cell death triggered by head trauma in developing rat brain. Proc Natl Acad Sci 96:2508.

Reinelt, H., Marx, T., Schirmer, U., Schmidt, M., 2001. Xenon expenditure and nitrogen accumulation in closed-circuit anaesthesia. Anaesthesia 56(4):309-311.

Riccio, A., Ginty, D. D., 2002. Nature Neurosci 5(5):389-390.

Rice, J. E., Vannucci, R. C., Brierley, J. B., 1981. The influence of immaturity on hypoxic-ischemic brain damage in the rat. Ann Neurol 9:131-141.

Rothman, S. M., Olney, J. W., 1986. Glutamate and the pathophysiology of hypoxic-ischemic brain damage. Ann Neurol 19:105-111.

Sanders, R. D., Franks, N. P., Maze, M., 2003. Xenon: no stranger to anaesthesia. BJA 91(5):709-717.

Sattler, R., Xiong, Z., Lu, W., MacDonald, J. F., Tymianski, M., 2000. Distinct roles of synaptic and extrasynaptic NMDA receptors in excitotoxicity. J Neurosci 20(1):22-33.

Shichino, T., Murakawa, M., Adachi, T., Miyazaki, Y., Segawa, H., Fukuda, K., Mori, K., 2002. Effects of xenon on acetylcholine release in the rat cerebral cortex in vivo. British Journal of Anaesthesia 88(6):866-868.

Talbot, J. H., 1941. The physiologic and therapeutic effects of hypothermia. N Eng J Med 224:281.

Taylor, D. L., Mehmet, H., Cady, E. B., Edwards, A. D., 2002. Improved neuroprotection with hypothermia delayed by 6 hours following cerebral hypoxia-ischemia in the 14-day-old rat. Ped Res 51(1):13-19.

Towfighi, J., Housman, C., Heitjan, D. F., Vannucci, R. C., Yager, J. Y., 1994. The effect of focal cerebral cooling on perinatal hypoxic-ischemic brain damage. Acta Neuropathol (Berl.) 87:598-604.

Treschera, W. H., Ishiwac, S., Johnston, M. V., 1997. Brief post-hypoxic-ischemic hypothermia markedly delays neonatal brain injury. Brain and Development 19:326-338.

Vannucci, R. C., 1997. Hypoxia-ischemia: Clinical Aspects in: Fanaroff, A. A., Martin, R. J., (Eds), Neonatal-perinatal medicine IV, Mosby-Yearbook Inc, Philadelphia, pp 877-891.

Vannucci, R. C., Connor, J. R., Mauger, D. T., Palmer, C., Smith, M. B., Towfighi, J., Vannucci, S. J., 1999. Mini-Review: Rat model of perinatal hypoxic-ischemic brain damage. J Neuro Res 55:158-163.

Vannucci, R. C., Perlman, J. M., 1997. Interventions for perinatal hypoxic-ischemic encephalopathy. Pediatrics 100(6): 1004-1014.

Volpe, 2001. Mental Retardation and Developmental Disabilities Research Reviews 7: 56-64.

Wilhelm, S., Ma, D., Maze, M., Franks, N. P., 2002. Effects of xenon on in vitro and in vivo models of neuronal injury. Anesthesiology 96:1485-1491.

Wyllie, A. H., Kerr, J. F. R., Currie, A. R., 1980. Cell death: the significance of apoptosis. Int Rev Cytol 68:251-306.

Windle, W F, 1969. Brain Damage by Asphyxia at Birth. Scientific American October; 221(4):76-84.

Xu, L., Yenari, M. A., Steinberg, G. K., Giffard, R. G., 2002. Mild hypothermia reduces apoptosis of mouse neurons in vitro early in the cascade. J Cereb Blood Flow Metab 22:21-28.

Yager, J. Y., Asselin, J., 1996. Effect of mild hypothermia on cerebral energy metabolism during the evolution of hypoxic-ischemic brain damage in the immature rat. Stroke 27:919-926.

The invention claimed is:

1. A method of treating neonatal asphyxia in a mammal in need thereof said method comprising: (a) administering to a mammal a gaseous mixture comprising xenon, the xenon having a percent concentration by volume of between about 12.5% and 50%; and (b) subjecting the mammal to hypothermia at temperatures between about 23° C. and 37° C.

2. A method according to claim 1 wherein the mammal is a human.

3. A method according to claim 1 wherein the xenon is administered in combination with a pharmaceutically acceptable carrier, diluent or excipient.

4. A method according to claim 1 wherein the xenon is administered in the form of a 20 to 70% v/v xenon/air mixture.

5. A method according to claim 1 wherein the xenon is administered simultaneously with hypothermia.

6. A method according to claim 1 wherein the xenon is administered separately from hypothermia.

7. A method according to claim 1 wherein the temperature of the mammal is maintained at a temperature of from about 32° C. to about 36° C.

8. A method according to claim 7 wherein the temperature of the mammal is maintained at a temperature of from about 33° C. to about 35° C.

9. A method according to claim 1 wherein the hypothermia is maintained for a period of at least 6 hours after the hypoxic-ischemic (HI) insult.

10. A method according to claim 1 wherein the hypothermia is maintained for a period of from about 6 to about 24 hours after the hypoxic-ischemic (HI) insult.

11. A method according to claim 1 wherein the xenon is administered to the mother of the mammal prior to birth.

12. A method according to claim 11 wherein the xenon is administered to the mother of the mammal prior to, or during, labour.

13. A method according to claim 11 wherein the xenon is administered to the mother of the mammal for up to about 24 hours prior to birth.

14. A method according to claim 1 wherein the xenon is administered in a therapeutically effective amount.

15. A method according to claim 1 wherein the xenon is administered in a sub-therapeutically effective amount.

16. A method according to claim 1 wherein the xenon is administered in a combination with an anesthetic selected from the group consisting of isoflurane, sevoflurane and desfiurane.

17. A method of treating neonatal asphyxia in a mammal in need thereof, said method comprising: (a) administering to the mother of the mammal prior to and/or during labour a gaseous mixture comprising xenon, the xenon having a percent concentration by volume of between about 12.5% and 50%; and (b) subjecting the mammal to hypothermia after birth at temperatures between about 23° C. and 37° C.

18. The method of claim 1, wherein the xenon is administered sequentially with hypothermia.

19. The method of claim 17, wherein the xenon is administered in a therapeutically effective amount.

20. The method according to claim 17, wherein the xenon is administered in a sub-therapeutically effective amount.

* * * * *

UNITED STATES PATENT AND TRADEMARK OFFICE
CERTIFICATE OF CORRECTION

PATENT NO. : 7,390,508 B2
APPLICATION NO. : 10/573093
DATED : June 24, 2008
INVENTOR(S) : Franks et al.

It is certified that error appears in the above-identified patent and that said Letters Patent is hereby corrected as shown below:

Column 20, line 16, change "33°c." to --33°C.--;

Column 22, line 17, change "Fberspäicher" to --Fberspächer--;

Column 23, line 30, change "chamey" to --charney--;

Column 24, lines 11-12, change "hippocarnpal" to --hippocampal--;

Column 25, line 32, change "A method" to --The method--;

Column 25, line 32, change "A method" to --The method--;

Column 25, line 34, change "A method" to --The method--;

Column 25, line 37, change "A method" to --The method--;

Column 25, line 40, change "A method" to --The method--;

Column 25, line 42, change "A method" to --The method--;

Column 26, line 1, change "A method" to --The method--;

Column 26, line 4, change "A method" to --The method--;

Column 26, line 7, change "A method" to --The method--;

Column 26, line 10, change "A method" to --The method--;

Column 26, line 13, change "A method" to --The method--;

Column 26, line 15, change "A method" to --The method--;

Column 26, line 18, change "A method" to --The method--;

Column 26, line 21, change "A method" to --The method--;

Column 26, line 23, change "A method" to --The method--;

UNITED STATES PATENT AND TRADEMARK OFFICE
CERTIFICATE OF CORRECTION

PATENT NO. : 7,390,508 B2
APPLICATION NO. : 10/573093
DATED : June 24, 2008
INVENTOR(S) : Franks et al.

It is certified that error appears in the above-identified patent and that said Letters Patent is hereby corrected as shown below:

Column 26, line 25, change "A method" to --The method--;

Column 26, line 27, change "desfiurane" to --desflurane--;

Column 26, line 28, change "desfiurane" to --desflurane--;

Signed and Sealed this

Twentieth Day of October, 2009

David J. Kappos
*Director of the United States Patent and Trademark Office*